(12) United States Patent
Desai et al.

(10) Patent No.: US 7,771,751 B2
(45) Date of Patent: Aug. 10, 2010

(54) COMPOSITIONS COMPRISING POORLY WATER SOLUBLE PHARMACEUTICAL AGENTS AND ANTIMICROBIAL AGENTS

(75) Inventors: Neil P. Desai, Los Angeles, CA (US); Raj Selvaraj, Lisle, IL (US); Andrew Yang, Rosemead, CA (US); Patrick Soon-Shiong, Los Angeles, CA (US)

(73) Assignee: Abraxis Bioscience, LLC, Los Angeles, CA (US)

( * ) Notice: Subject to any disclaimer, the term of this patent is extended or adjusted under 35 U.S.C. 154(b) by 0 days.

(21) Appl. No.: 11/514,030

(22) Filed: Aug. 30, 2006

(65) Prior Publication Data

US 2007/0117744 A1 May 24, 2007

Related U.S. Application Data

(60) Provisional application No. 60/712,865, filed on Aug. 31, 2005, provisional application No. 60/736,962, filed on Nov. 14, 2005, provisional application No. 60/736,931, filed on Nov. 14, 2005.

(51) Int. Cl.
*A61K 9/50* (2006.01)
*A61K 9/14* (2006.01)
*A61K 9/00* (2006.01)

(52) U.S. Cl. ............... 424/499; 977/702; 977/705; 977/773; 977/788; 424/489; 424/400

(58) Field of Classification Search ........... 514/776, 514/2; 424/499
See application file for complete search history.

(56) References Cited

U.S. PATENT DOCUMENTS

| | | | |
|---|---|---|---|
| 4,826,689 A | 5/1989 | Violanto | |
| 4,960,799 A | 10/1990 | Nagy | |
| 5,118,528 A | 6/1992 | Fessi et al. | |
| 5,145,684 A | 9/1992 | Liversidge et al. | |
| 5,334,582 A | 8/1994 | Blackburn et al. | |
| 5,362,478 A | 11/1994 | Desai et al. | |
| 5,439,686 A | 8/1995 | Desai et al. | |
| 5,498,421 A | 3/1996 | Grinstaff et al. | |
| 5,637,625 A | 6/1997 | Haynes | |
| 5,639,473 A | 6/1997 | Grinstaff et al. | |
| 5,650,156 A | 7/1997 | Grinstaff et al. | |
| 5,665,382 A | 9/1997 | Grinstaff et al. | |
| 5,665,383 A | 9/1997 | Grinstaff et al. | |
| 5,681,846 A | 10/1997 | Trissel | |
| 5,714,520 A | 2/1998 | Jones et al. | |
| 5,725,804 A | 3/1998 | Yen | |
| 5,731,355 A | 3/1998 | Jones et al. | |
| 5,731,356 A | 3/1998 | Jones et al. | |
| 5,731,366 A | 3/1998 | Moench et al. | |
| 5,731,556 A | 3/1998 | Gardner et al. | |
| 5,733,888 A | 3/1998 | Carver et al. | |
| 5,770,222 A | 6/1998 | Unger et al. | |
| 5,908,869 A | 6/1999 | Jones et al. | |
| 5,916,596 A | 6/1999 | Desai et al. | |
| 5,977,164 A | 11/1999 | Carver et al. | |
| 5,997,904 A | 12/1999 | Magdassi et al. | |
| 6,022,985 A | 2/2000 | Authelin et al. | |
| 6,028,108 A * | 2/2000 | George | 514/564 |
| 6,071,974 A | 6/2000 | Patel et al. | |
| 6,090,844 A | 7/2000 | Han et al. | |
| 6,096,331 A | 8/2000 | Desai et al. | |
| 6,100,302 A | 8/2000 | Pejaver et al. | |
| 6,120,805 A | 9/2000 | Spenlehauer et al. | |
| 6,140,373 A | 10/2000 | May et al. | |
| 6,140,374 A | 10/2000 | May et al. | |
| 6,147,122 A | 11/2000 | Mirejovsky et al. | |
| 6,150,423 A | 11/2000 | Carpenter | |
| 6,177,477 B1 | 1/2001 | George et al. | |
| 6,217,886 B1 | 4/2001 | Önyüksel et al. | |
| 6,326,406 B1 | 12/2001 | De Tommaso | |
| 6,399,087 B1 | 6/2002 | Zhang et al. | |
| 6,469,069 B1 | 10/2002 | Mirejovsky et al. | |
| 6,506,405 B1 | 1/2003 | Desai et al. | |
| 6,534,547 B1 | 3/2003 | Carpenter | |
| 6,537,539 B2 | 3/2003 | Li et al. | |
| 6,537,579 B1 | 3/2003 | Desai et al. | |

(Continued)

FOREIGN PATENT DOCUMENTS

EP   1 348 430 A1   10/2003

(Continued)

OTHER PUBLICATIONS

U.S. Appl. No. 09/446,783, filed May 16, 2000, Desai et al.

(Continued)

*Primary Examiner*—Ruth A Davis
*Assistant Examiner*—Sheridan R MacAuley
(74) *Attorney, Agent, or Firm*—Morrison & Foerster, LLP

(57) ABSTRACT

The present invention provides compositions comprising a poorly water soluble pharmaceutical agent, a carrier protein, and an antimicrobial agent, wherein significant microbial growth is inhibited in the composition. The amount of the antimicrobial agent in the composition may be below the level that induces a toxicological effect or at a level where a potential side effect can be controlled or tolerated. Also provided are compositions comprising a poorly water soluble pharmaceutical agent, a carrier protein, a sugar, and optionally an antimicrobial agent. Methods of using the compositions are also provided.

21 Claims, No Drawings

U.S. PATENT DOCUMENTS

| | | |
|---|---|---|
| 6,610,317 B2 | 8/2003 | Straub et al. |
| 6,638,537 B2 | 10/2003 | Dennis et al. |
| 6,652,884 B2 | 11/2003 | Falciani |
| 6,726,919 B2 | 4/2004 | Pace et al. |
| 6,743,436 B1 | 6/2004 | Lee et al. |
| 6,749,868 B1 | 6/2004 | Desai et al. |
| 6,753,006 B1 | 6/2004 | Desai et al. |
| 6,838,569 B2 | 1/2005 | Sharma et al. |
| 6,914,130 B2 | 7/2005 | Gao et al. |
| 6,919,370 B2 | 7/2005 | Chen |
| 7,041,705 B2 | 5/2006 | Mishra et al. |
| 7,060,285 B2 | 6/2006 | Muller |
| 7,060,724 B2 | 6/2006 | Li et al. |
| 7,175,850 B2 | 2/2007 | Cevc |
| 7,332,568 B2 | 2/2008 | Trieu et al. |
| 2002/0039594 A1 | 4/2002 | Unger |
| 2002/0041897 A1 | 4/2002 | Dang |
| 2002/0159952 A1 | 10/2002 | Unger |
| 2003/0099674 A1 | 5/2003 | Chen |
| 2003/0157161 A1 | 8/2003 | Hunter et al. |
| 2003/0185894 A1 | 10/2003 | Zenoni et al. |
| 2003/0187062 A1 | 10/2003 | Zenoni et al. |
| 2003/0199425 A1 | 10/2003 | Desai et al. |
| 2004/0009168 A1 | 1/2004 | Kaisheva et al. |
| 2004/0097417 A1 | 5/2004 | DeYoung et al. |
| 2004/0105821 A1 | 6/2004 | Bernstein et al. |
| 2004/0116720 A1 | 6/2004 | Sharma et al. |
| 2004/0126360 A1 | 7/2004 | Manning et al. |
| 2004/0143004 A1 | 7/2004 | Fargnoli et al. |
| 2004/0171560 A1 | 9/2004 | Mukherjee et al. |
| 2004/0204372 A1 | 10/2004 | Cohen et al. |
| 2005/0004002 A1 | 1/2005 | Desai et al. |
| 2005/0019266 A1 | 1/2005 | Unger et al. |
| 2005/0043272 A1* | 2/2005 | Platt et al. ............ 514/54 |
| 2005/0152979 A1 | 7/2005 | Besman et al. |
| 2005/0238649 A1 | 10/2005 | Doronina et al. |
| 2006/0073175 A1 | 4/2006 | Soon-Shiong et al. |
| 2006/0079672 A1 | 4/2006 | Glidden |
| 2006/0083782 A1 | 4/2006 | Desai et al. |
| 2006/0121119 A1 | 6/2006 | Zenoni et al. |
| 2006/0127445 A1 | 6/2006 | Hunter et al. |
| 2006/0199248 A1 | 9/2006 | Trieu et al. |
| 2006/0217436 A1 | 9/2006 | Li et al. |
| 2006/0241170 A1 | 10/2006 | Soon-Shiong et al. |
| 2006/0257326 A1 | 11/2006 | Desai et al. |
| 2006/0263434 A1 | 11/2006 | Desai et al. |
| 2007/0020337 A1 | 1/2007 | Zenoni et al. |
| 2007/0025910 A1 | 2/2007 | Norenberg |
| 2007/0082838 A1 | 4/2007 | De et al. |
| 2007/0087022 A1 | 4/2007 | Desai et al. |
| 2007/0092563 A1 | 4/2007 | Desai et al. |
| 2007/0093547 A1 | 4/2007 | Desai et al. |
| 2007/0116761 A1 | 5/2007 | Desai et al. |
| 2007/0116774 A1 | 5/2007 | Desai et al. |
| 2007/0117133 A1 | 5/2007 | Trieu et al. |
| 2007/0117744 A1 | 5/2007 | Desai et al. |
| 2007/0117862 A1 | 5/2007 | Desai et al. |
| 2007/0117863 A1 | 5/2007 | Desai et al. |
| 2007/0122465 A1 | 5/2007 | Desai et al. |
| 2007/0122468 A1 | 5/2007 | Desai et al. |
| 2007/0128290 A1 | 6/2007 | Desai et al. |
| 2007/0129448 A1 | 6/2007 | Desai et al. |
| 2007/0142457 A1 | 6/2007 | Pontiroli et al. |
| 2007/0166388 A1 | 7/2007 | Desai et al. |
| 2007/0191473 A1 | 8/2007 | Desai et al. |
| 2007/0196361 A1 | 8/2007 | Soon-Shiong et al. |
| 2008/0146651 A1 | 6/2008 | Jee et al. |
| 2008/0166389 A1 | 7/2008 | Desai et al. |
| 2008/0213370 A1 | 9/2008 | Desai et al. |
| 2008/0280987 A1 | 11/2008 | Desai et al. |
| 2009/0048331 A1 | 2/2009 | Soon-Shiong et al. |
| 2009/0098210 A1 | 4/2009 | Desai et al. |
| 2009/0196933 A1 | 8/2009 | De et al. |
| 2009/0263483 A1 | 10/2009 | Desai et al. |

FOREIGN PATENT DOCUMENTS

| | | |
|---|---|---|
| EP | 0 835 657 B1 | 8/2004 |
| WO | WO-94/12031 A1 | 6/1994 |
| WO | WO-94/12198 A1 | 6/1994 |
| WO | WO 94/18954 A1 | 9/1994 |
| WO | WO-97/33552 A1 | 9/1997 |
| WO | WO 97/49390 A1 | 12/1997 |
| WO | WO 98/14174 A1 | 4/1998 |
| WO | WO 98/14175 A1 | 4/1998 |
| WO | WO 98/23646 A2 | 6/1998 |
| WO | WO 98/23646 A3 | 6/1998 |
| WO | WO 98/45331 A2 | 10/1998 |
| WO | WO 98/45331 A3 | 10/1998 |
| WO | WO 99/00113 A1 | 1/1999 |
| WO | WO 99/12640 A1 | 3/1999 |
| WO | WO-99/33780 A1 | 7/1999 |
| WO | WO 99/39696 A1 | 8/1999 |
| WO | WO-99/43344 A2 | 9/1999 |
| WO | WO-99/43344 A3 | 9/1999 |
| WO | WO 00/06152 A1 | 2/2000 |
| WO | WO-00/23050 A1 | 4/2000 |
| WO | WO 00/40269 A2 | 7/2000 |
| WO | WO 00/40269 A3 | 7/2000 |
| WO | WO 00/44369 A1 | 8/2000 |
| WO | WO 00/59472 A1 | 10/2000 |
| WO | WO 00/71079 A1 | 11/2000 |
| WO | WO-01/15675 A2 | 3/2001 |
| WO | WO-01/15675 A3 | 3/2001 |
| WO | WO 01/37808 A1 | 5/2001 |
| WO | WO-01/72299 A1 | 10/2001 |
| WO | WO-01/72300 A1 | 10/2001 |
| WO | WO 01/89522 A1 | 11/2001 |
| WO | WO 02/079748 A2 | 10/2002 |
| WO | WO 02/079748 A3 | 10/2002 |
| WO | WO 02/087545 A1 | 11/2002 |
| WO | WO 03/017977 A1 | 3/2003 |
| WO | WO-03/047577 A2 | 6/2003 |
| WO | WO-03/047577 A3 | 6/2003 |
| WO | WO-03/053350 A2 | 7/2003 |
| WO | WO-03/053350 A3 | 7/2003 |
| WO | WO 03/096944 A1 | 11/2003 |
| WO | WO 2004/078747 A1 | 9/2004 |
| WO | WO 2004/094476 A1 | 11/2004 |
| WO | WO 2005/000900 A1 | 1/2005 |
| WO | WO 2005/051444 A2 | 6/2005 |
| WO | WO 2005/052116 A2 | 6/2005 |
| WO | WO 2005/052116 A3 | 6/2005 |
| WO | WO-2005/115531 A2 | 12/2005 |
| WO | WO-2005/115531 A3 | 12/2005 |
| WO | WO 2006/069388 A2 | 6/2006 |
| WO | WO 2006/069388 A3 | 6/2006 |
| WO | WO 2006/089290 A1 | 8/2006 |
| WO | WO 2006/091780 A2 | 8/2006 |
| WO | WO 2006/091780 A3 | 8/2006 |
| WO | WO-2006/133510 A1 | 12/2006 |
| WO | WO 2007/027819 A2 | 3/2007 |
| WO | WO 2007/027819 A3 | 3/2007 |
| WO | WO 2007/027941 A2 | 3/2007 |
| WO | WO 2007/027941 A3 | 3/2007 |
| WO | WO-2007/044950 A2 | 4/2007 |
| WO | WO-2007-044950 A3 | 4/2007 |
| WO | WO-2007/096900 A1 | 8/2007 |
| WO | WO-2007/109654 A2 | 9/2007 |
| WO | WO-2007/109654 A3 | 9/2007 |

OTHER PUBLICATIONS

U.S. Appl. No. 09/937,840, filed Jan. 28, 2002, Desai et al.
U.S. Appl. No. 11/553,339, filed Oct. 26, 2006, Desai et al.

U.S. Appl. No. 11/644,850, filed Dec. 22, 2006, Desai et al.
U.S. Appl. No. 11/833,179, filed Aug. 2, 2007, Desai et al.
U.S. Appl. No. 11/833,188, filed Aug. 2, 2007, Desai et al.
U.S. Appl. No. 11/880,218, filed Jul. 19, 2007, Desai et al.
U.S. Appl. No. 11/880,314, filed Jul. 20, 2007, Desai et al.
U.S. Appl. No. 11/890,006, filed Aug. 3, 2007, Desai et al.
U.S. Appl. No. 11/890,041, filed Aug. 3, 2007, Desai et al.
U.S. Appl. No. 11/890,197, filed Aug. 3, 2007, Desai et al.
U.S. Appl. No. 11/890,603, filed Aug. 6, 2007, Desai et al.
U.S. Appl. No. 11/890,639, filed Aug. 6, 2007, Desai et al.
U.S. Appl. No. 11/890,648, filed Aug. 6, 2007, Desai et al.
U.S. Appl. No. 11/890,599, filed Aug. 6, 2007, Desai et al.
U.S. Appl. No. 11/890,819, filed Aug. 7, 2007, Desai et al.
Baker, M. T. et al. (Oct. 2005). "Propofol: The Challenges of Formulation," *Anesthesiology* 103(4):860-876.
Baker, M.T. (Jun. 1, 2001). "Yellowing of Metabisulfate-Containing Propofol Emulsion," *Am. J. Health Syst. Pharm.* 58:1042, 1044, 1046, 1047.
Bissery, M.-C. et al. (Sep. 15, 1991). "Experimental Antitumor Activity of Taxotere (RP 56976, NSC 628503), a Taxol Analogue," *Cancer Res.* 51(18):4845-4852.
Briggs, L. P. et al. (1982). "An Adverse Reaction to the Administration of Disoprofol (Diprivan)," *Anesthesia* 37:1099-1101.
Cortes, J. E. et al. (Oct. 1995). "Docetaxel," *J. Clin. Oncol.* 13(10):2643-2655.
Desai, N.P. et al. (Sep. 2004). "Increased Transport of Nanoparticle Albumin-Bound Paclitaxel (ABI-007) by Endothelial gp60-Mediated Caveolar Transcytosis: A Pathway Inhibited by Taxol," *European Journal of Cancer, Abstract, 16th EORT-NCI-AACR Symposium on Molecular Targets and Cancer Therapeutics*, Geneva, Switzerland. 2(8):182, Poster No. 601.
Dykes, D. J. et al. (1995). "Response of Human Tumor Xenografts in Athymic Nude Mice to Docetaxel, (RP 56976, Taxotere®)" *Investigational New Drugs* 13:1-11.
Fehske, K. J. et al. (Jan. 1, 1981). "The Location of Drug Binding Sites in Human Serum Albumin," *Biochemical Pharmacology* 30(7):687-692.
Finlayson, J. S. (1980). "Albumin Products," *Seminars in Thrombosis and Hemostasis* 6(2):85-120.
Flournoy, D. J. (Jul. 1991). "In Vitro Antimicrobial Properties of Deferoxamine Mesylate," *European Journal of Clinical Microbiology & Infectious Diseases* 10(7):597-598.
Garrido, M. J. et al. (Nov.-Dec. 1994). "Caraterización de la Fijación de Propofol a Las Proteinas Plasmáticas y Posibles Interacciones," *Rev. Esp. Anestesiol. Reanim.* 41(6):308-312.
Gelderblom, H. et al. (2001). "Cremophor EL: The Drawbacks And Advantages of Vehicle Selection for Drug Formulation," *Eur. J. of Cancer* 37:1590-1598.
Gupta, S. et al. (Apr. 4, 2003). "Development of a Multidose Formulation for a Humanized Monoclonal Antibody Using Experimental Design Techniques," *AAPS PharmSci* 5(2):1-9.
Joint FAO/WHO Expert Committee on Food Additives. (1971). "A Review of the Technological Efficacy of Some Antimicrobial Agents," *FAO Nutritional Meetings Reports Series No. 48C WHO/FOOD Add./70/41* pp. 1-61.
Lam, X. M. et al. (Jun. 1997). "The Effect of Benzyl Alcohol on Recombinant Human Interferon-Y," *Pharm. Res.* 14(6):725-729.
Mollison, P. L. (Jan. 2000). "The Introduction of Citrate as an Anticoagulant for Transfusion and of Glucose as a Red Cell Preservative," *British Journal of Haematology* 108(1):13-18.
Paál, K. et al. (2001). "High Affinity Binding of Paclitaxel to Human Serum Albumin." *Eur. J. Biochem.* 268:2187-2191.
Purcell, M. et al. (2000). "Interaction of Taxol with Human Serum Albumin," *Biochimica et Biophysica Acta* 1478:61-68.
Sharma, U. S. et al. (Oct. 1995). "Pharmaceutical and Physical Properties of Paclitaxel (Taxol) Complexes With Cyclodextrins," *J. Pharm. Sci.*, 84(10):1223-1230.
Sharma, A. et al. (Dec. 1995). "Antitumor Efficacy of Taxane Liposomes on a Human Ovarian Tumor Xenograft in Nude Athymic Mice," *J. Pharm. Sci.* 84(12):1400-1404.
Sharma, A. et al. (1996). "Paclitaxel-Liposomes for Intracavitary Therapy of Intraperitoneal P388 Leukemia," *Cancer Lett.* 107(2):265-272.

Shimoni, E. et al. (Jun. 1994). "Antioxidant Properties of Deferoxamine," *Journal of the American Oil Chemists' Society* 71(6):641-644.
Straubinger, R. M. et al. (1993). "Novel Taxol Formulations: Taxol-Containing Liposomes," *J. Natl. Cancer Inst. Monogr.* (15):69-78.
Sutton, S. V. W. et al. (Nov./Dec. 2002). "Development of the Antimicrobial Effectiveness Test as USP Chapter <51>," *PDA Journal of Pharmaceutical Science and Technology* 56(6):300-311.
Tullis, J. L. (Jan. 24, 1977). "Albumin 1. Background and Use," *The Journal of the American Medical Association* 237(4):355-360, 460-463.
Urien, S. et al. (1996). "Docetaxel Serum Protein Binding with High Affinity to Alpha$_1$-Acid Glycoprotein," *Investigational New Drugs* 14(2):147-151.
Vorum, H. (Nov. 1999). "Reversible Ligand Binding to Human Serum Albumin," *Danish Medical Bulletin* 46(5):379-399.
Waugh, W. N. et al. (Jul. 1991). "Stability, Compatibility, and Plasticizer Extraction of Taxol (NSC-125973) Injection Diluted in Infusion Solutions and Stored in Various Containers," *Am. J. Hosp. Pharmacists* 48(7):1520-1524.
Wooley, R. E. et al. (Jun. 1983). "Action of EDTA-Tris and Antimicrobial Agent Combinations on Selected Pathogenic Bacteria," *Vet Microbiol.* 8(3):271-280.
International Search Report mailed on Feb. 28, 2007, for PCT Patent Application No. PCT/&S2006/033931, filed on Aug. 30, 2006, four pages.
U.S. Appl. No. 11/890,819, filed on Aug. 7, 2007, for Desai et al.
U.S. Appl. No. 11/897,724, filed on Aug. 31, 2007, for Desai et al.
U.S. Appl. No. 12/051,782, filed on Mar. 19, 2008, for Desai et al.
Altmayer, P. et al. (1995). "Propofol Binding to Human Blood Proteins," *Arzneim. Forsc./Drug Res.* 45(II)(10):1053-1055.
Balasubramanian, S.V. et al. (1994). "Taxol-Lipid Interactions: Taxol-Dependent Effects on the Physical Properties of Model Membranes," *Biochemistry* 33:8941-8947.
Balasubramanian, S.V. et al. (Oct. 1994). "Solvent- and Concentration-Dependent Molecular Interactions of Taxol (Paclitaxel)," *J. Pharm. Sci.* 83(10):1470-1476.
Calabresi, P. et al. (1996). Introduction of "Chemotherapy of Neoplastic Disease," Section X, in *The Pharmacological Basis of Therapeutics*, 9$^{th}$ Edition, McGraw-Hill: New York, NY pp. 1225-1230.
Carter, D.C. et al. (1994). "Structures of Serum Albumin," in *Advances in Protein Chemistry*, vol. 45: Lipoprotein, Apolipoproteins, and Lipases, Schumaker, V.N., ed., Academic Press, Inc.: San Diego, CA, pp. 153-203.
Curry, S. et al. (Sep. 1998). "Crystal Structure of Human Serum Albumin Complexed with Fatty Acid Reveals an Asymmetric Distribution of Binding Sites," *Nat. Struct. Biol.* 5(9):827-835.
Davis, M.A. et al. (1978). "Pulmonary Perfusion Imaging: Acute Toxicity and Safety Factors as a Function of Particle Size," *J. Nucl Med.* 19(11):1209-1213.
Fehske, K.J. et al. (1981). "The Location of Drug Binding Sites in Human Serum Albumin," *Biochem. Pharmacol.* 30(7):687-692.
Hauser, C.J. et al. (Jun. 1980). "Oxygen Transport Responses to Colloids and Crystalloids in Critically Ill Surgical Patients," *Surg. Gynecol. Obstet.* 150(6):811-816.
He, X.M. et al. (Jul. 16, 1992). "Atomic Structure and Chemistry of Human Serum Albumin," *Nature* 358:209-215.
International Search Report mailed on Feb. 28, 2007, for International Application No. PCT/US2006/034103, filed on Aug. 30, 2006, four pages.
Keowmaneechai, E. et al. (Nov. 20, 2002). "Influence of EDTA and Citrate on Physicochemical Properties of Whey Protein-Stabilized Oil-in-Water Emulsions Containing CaCl$_2$," *J. Agric. Food Chem.* 50(24):7145-7153.
Kragh-Hansen, U. (Feb. 1990). "Structure and Ligand Binding Properties of Human Serum Albumin," *Dan. Med. Bull.* 37(1):57-84.
Schroeder, H.G. et al. (Apr. 1978). "Distribution of Radiolabeled Subvisible Microspheres after Intravenous Administration to Beagle Dogs," *J. Pharm Sci.* 67(4):504-507.
Schroeder, H.G. et al. (Apr. 1978). "Physiological Effects of Subvisible Microspheres Administered Intravenously to Beagle Dogs," *J. Pharm. Sci.* 67(4):508-513.

Sharma, A. et al. (Dec. 15, 1993). "Antitumor Effect of Taxol-Containing Liposomes in a Taxol-Resistant Murine Tumor Model," *Cancer Res.* 53(24):5877-5881.

Sharma, A. et al. (Jun. 1994). "Novel Taxol Formulations: Preparation and Characterization of Taxol-Containing Liposomes," *Pharm. Res.* 11(6):889-896.

Sugio, S. et al. (1999). "Crystal Structure of Human Serum Albumin at 2.5 Å Resolution," *Protein. Eng.* 12(6):439-446.

Tomiak, E. et al. (Jul. 1994). "Phase I Study of Docetaxel Administered as a 1-Hour Intravenous Infusion on a Weekly Basis," *J. Clin. Oncol.* 12(7):1458-1467.

Villiere, A. et al. (2005; e-pub. Feb. 12, 2005). "Oxidative Stability of Bovine Serum Albumin- and Sodium Caseinate-Stabilized Emulsions Depends on Metal Availability," *J. Agric. Food Chem.* 53(5):1514-1520.

Wolin, M.J. (May 1966). "Lysis of *Vibrio succinogenes* by Ethylenediamine-tetraacetic Acid or Lysozyme," *J. Bacteriol.* 91(5):1781-1786.

Yokel, R.A. et al. (1981). "Acute Toxicity of Latex Microspheres," *Toxicol. Lett.* 9:165-170.

U.S. Appl. No. 12/051,782, filed Mar. 19, 2008 for Desai et al.
U.S. Appl. No. 12/240,893, filed Sep. 29, 2008, for Desai et al.
U.S. Appl. No. 12/271,748, filed Nov. 14, 2008, for Desai et al.
U.S. Appl. No. 12/331,924, filed Dec. 10, 2008, for Desai et al.
U.S. Appl. No. 12/334,115, filed Dec. 12, 2008, for Desai et al.
U.S. Appl. No. 12/402,358, filed Mar. 11, 2009, for De et al.
U.S. Appl. No. 12/422,011, filed Apr. 10, 2009, for Desai et al.
U.S. Appl. No. 12/474,218, filed May 28, 2009 for Desai et al.
U.S. Appl. No. 12/436,697, filed May 6, 2009, for Desai et al.
U.S. Appl. No. 12/479,710, filed Jun. 5, 2009 for Desai et al.
U.S. Appl. No. 12/513,843, filed May 6, 2009, for Desai et al.
U.S. Appl. No. 12/519,126, filed Jun. 12, 2009 for Desai et al.
U.S. Appl. No. 12/530,188, internationally filed on Mar. 7, 2008 for Desai et al.
U.S. Appl. No. 12/598,406, internationally filed on May 5, 2008, for Desai et al.
U.S. Appl. No. 12/600,991, filed Nov. 19, 2009 for Desai et al.

Abraxis Oncology—A Division of American Pharmaceutical Partners, Inc. (Jan. 7, 2005). "Abraxane™ for Injectable Suspension (Paclitaxel Protein-Bound Particles for Injectable Suspension) (Albumin Bound)," *Patient Information Booklet approved by the Food and Drug Administration based on Abraxane Package Insert Version* 12, 26 pages total.

The United States Pharmacopeia Convention, Inc. (Dec. 1, 2009). "Paclitaxel," located at http://www.uspnf.com/uspnf/pub/data/v32272/usp32nf27s2_m60190.xml, last visited Jan. 21, 2010, 9 pages total.

Wilkinson, S. G. (1967). "The Sensitivity of Pseudomonas to Ethylene-Diaminetetra-Acetic Acid," *J. Gen. Microbiol.* 47:67-76.

\* cited by examiner

COMPOSITIONS COMPRISING POORLY WATER SOLUBLE PHARMACEUTICAL AGENTS AND ANTIMICROBIAL AGENTS

CROSS-REFERENCE TO RELATED APPLICATIONS

This application claims the priority benefit of U.S. Provisional Application 60/712,865 filed Aug. 31, 2005, U.S. Provisional Application 60/736,962 filed Nov. 14, 2005, and U.S. Provisional Application 60/736,931 filed Nov. 14, 2005, all of which are hereby incorporated herein by reference in their entireties.

TECHNICAL FIELD

This application pertains to compositions comprising protein-associated poorly water soluble pharmaceutical agents for parenteral or other uses, further comprising an antimicrobial agent.

BACKGROUND

Many drugs for parenteral use, especially those administered intravenously, cause undesirable side effects. These drugs are frequently water insoluble, and are thus formulated with solubilizing agents, surfactants, solvents, and/or emulsifiers that may be irritating, allergenic, or toxic when administered to patients (see, e.g., Briggs et al., *Anesthesis* 37:1099 (1982), and Waugh et al., *Am. J. Hosp. Pharmacists,* 48:1520 (1991)). For example, the chemotherapeutic drug paclitaxel is active against carcinomas of the ovary, breast, lung, esophagus and head and neck. Paclitaxel, however, has been shown to induce toxicities associated with administration, as well as significant acute and cumulative toxicity, such as myelosuppression, neutropenic fever, anaphylactic reaction, and peripheral neuropathy. Paclitaxel is very poorly water soluble, and as a result, cannot be practically formulated with water for IV administration. Traditionally, paclitaxel is formulated for IV administration in a solution with polyoxyethylated castor oil (Cremophor) as the primary solvent and high concentrations of ethanol as cosolvent. Cremophor is associated with side effects that can be severe, including anaphylaxis and other hypersensitivity reactions that require pretreatment with corticosteroids, antihistamines, and $H_2$ blockers (see, e.g., Gelderblom et al., *Eur. J. of Cancer,* 37:1590-1598, (2001)). Similarly, docetaxel is used in treatment of anthracycline-resistant breast cancer, but also has been shown to induce side effects of hypersensitivity and fluid retention that can be severe.

To circumvent problems associated with administration-related side effects of drug formulations, alternative formulations have been developed. For example, Abraxane™ is a Cremophor-free, protein stabilized formulation of paclitaxel that was developed to resolve or minimize side effects caused by the Cremophor EL/ethanol formulation. Similar protein-containing formulations have also been developed for other taxanes such as docetaxel and ortataxel, as well as other drugs.

Because protein serves as a good substrate for microbial growth, one major challenge encountered when using these protein-containing formulations is potential microbial contamination. For example, in order to minimize the risk of microbial contamination, the current intravenous formulation of Abraxane™ is stored in lyophilized form, and should be injected immediately (e.g., within hours) after it is reconstituted in an aqueous medium. Bacterial growth can result from inadvertent contamination in a container containing a single dosage. Bacterial contamination is even more of a problem when multiple dosage withdrawals from the containers are needed.

Antibacterial agents such as EDTA, pentetate, or sulfites containing agents are generally known and used in pharmaceutical compositions. See, e.g., U.S. Pat. Nos. 5,714,520, 5,731,355, 5,731,356, 6,028,108, 6,100,302, 6,147,122, 6,177,477, 6,399,087, and 6,469,069, International Patent Application No. WO 99/39696, and U.S. Pat. Pub. No. 20050004002. Many of the antibacterial agents, however, are considerably toxic. For example, the addition of sulfites to drug formulations present potential adverse effects to the pediatric population and for those in the general population who are allergic to sulfur. See, e.g., Baker et al., *Anesthesiology,* 103(4):1-17 (2005); Mirejovsky, *Am. J. Health Syst. Pharm.,* 58:1047 (2001). The toxicities of these antibacterial agents become a significant problem in formulating protein-containing pharmaceutical drug compositions, which frequently require more antimicrobial agents than non-protein containing formulations do in order to counter significant microbial growth therein.

Furthermore, many antimicrobial agents are known to interact with proteins and cause stability problems such as aggregation. See, e.g., Lam et al., *Pharm. Res.* 14:725-729 (1997). The effect of antimicrobial agents on protein stability raises a difficult issue in formulating protein-containing compositions of poorly water soluble pharmaceutical agents, since proper configuration of proteins is generally required for stabilizing poorly water soluble pharmaceutical agents in the composition.

There is therefore a need to develop protein-containing formulations of poorly water soluble pharmaceutical agents which contain antimicrobial agents that provide a desired antimicrobial efficacy but do not significantly affect protein stability and/or do not cause unacceptable toxicological effects upon administration. There is also a need to develop protein-containing formulations of poorly water soluble pharmaceutical agents that can be more readily reconstituted.

The disclosures of all publications, patents, patent applications and published patent applications referred to herein are hereby incorporated herein by reference in their entireties.

BRIEF SUMMARY OF THE INVENTION

The invention provides compositions (such as pharmaceutical compositions) comprising a poorly water soluble pharmaceutical agent, a carrier protein (such as albumin, for example, human serum albumin (HSA)), and an antimicrobial agent, wherein significant microbial growth is inhibited in the composition. In some embodiments, significant microbial growth in the compositions is inhibited for a given period of time, such as at least about 4 hours (including for example at least about any of 8, 12, 16, 24, 36, 48, 60, 72, 84, 96, 108, or 120 hours). In some embodiments, the compositions are less susceptible to microbial contamination as compared to compositions not containing an antimicrobial agent. In some embodiments, the compositions of the invention comprise a poorly water soluble pharmaceutical agent, a carrier protein (such as albumin, for example HSA), and an antimicrobial agent, wherein the antimicrobial agent is in an amount effective to inhibit significant microbial growth in the composition(s).

In some embodiments, the poorly water soluble pharmaceutical agent is an antineoplastic agent or a chemotherapeutic agent. In some embodiments, the poorly water soluble pharmaceutical agent is any of (and in some embodiments selected from the group consisting of) paclitaxel, docetaxel, ortataxel or other taxanes, geldanamycin, 17-allyl amino geldanamycin, thiocolchicine and its dimers, rapamycin, cyclosporine, epothilone, radicicol, and combretastatin. For example, in some embodiments, there is provided a composition comprising a taxane or a derivative thereof (such as paclitaxel, docetaxel, or ortataxel), a carrier protein (such as albumin, for example HSA), and an antimicrobial agent, wherein significant microbial growth is inhibited in the composition. In some embodiments, there is provided a composition comprising a taxane or a derivative thereof (such as paclitaxel, docetaxel, or ortataxel), a carrier protein (such as albumin, for example HSA), and an antimicrobial agent, wherein the antimicrobial agent is in an amount effective to inhibit significant microbial growth in the composition. In some embodiments, the poorly water soluble pharmaceutical agent is an amorphous and/or non-crystalline taxane (such as paclitaxel). In some embodiments, the poorly water soluble pharmaceutical agent used to make the composition is in an anhydrous form (such as anhydrous docetaxel). In some embodiments, the antimicrobial agent is not deferoxamine (i.e., is other than deferoxamine).

In some embodiments, there is provided a composition comprising a poorly water soluble pharmaceutical agent, a carrier protein (such as albumin, for example HSA), and an antimicrobial agent, wherein the antimicrobial agent is a chelating agent, and wherein significant microbial growth is inhibited in the composition. In some embodiments, there is provided a composition comprising a taxane or a derivative thereof (such as paclitaxel, docetaxel, or ortataxel), a carrier protein (such as albumin, for example HSA), and an antimicrobial agent, wherein the antimicrobial agent is a chelating agent, and wherein significant microbial growth is inhibited in the composition. In some embodiments, the antimicrobial agent is a polydentate chelating agent. In some embodiments, the antimicrobial agent comprises one or more carboxylic acid groups. In some embodiments, the chelating agent is not deferoxamine (i.e., is other than deferoxamine). In some embodiments, the chelating agent is any of (and in some embodiments selected from the group consisting of) edetate, citrate, pentetate, tromethamine, sorbate, ascorbate, derivatives thereof, and mixtures thereof. In some embodiments, the chelating agent comprises citrate and EDTA.

In some embodiments, there is provided a composition comprising a poorly water soluble pharmaceutical agent, a carrier protein (such as albumin, for example HSA), and an antimicrobial agent, wherein the antimicrobial agent is a non-chelating agent, and wherein significant microbial growth is inhibited in the composition. In some embodiments, there is provided a composition comprising a taxane or a derivative thereof (such as paclitaxel, docetaxel, or ortataxel), a carrier protein (such as albumin, for example HSA), and an antimicrobial agent, wherein the antimicrobial agent is a non-chelating agent, and wherein significant microbial growth is inhibited in the composition. In some embodiments, the non-chelating antimicrobial agent functions as pro-oxidant. In some embodiments, the non-chelating antimicrobial agent functions as an antioxidant. In some embodiments, the non-chelating agent is any of (and in some embodiments selected from the group consisting of) sulfites, benzoic acid, benzyl alcohol, chlorobutanol, paraben, and derivatives thereof.

In some embodiments, the composition comprises a poorly water soluble pharmaceutical agent, an albumin, and an antimicrobial agent, wherein the weight ratio of the albumin to the poorly water soluble pharmaceutical agent in the composition is about 0.01:1 to about 100:1, and wherein significant microbial growth is inhibited in the composition. In some embodiments, the composition comprises a poorly water soluble pharmaceutical agent, an albumin, and an antimicrobial agent, wherein the weight ratio of the albumin to the poorly water soluble pharmaceutical agent in the composition is about 18:1 or less (including for example any of about 1:1 to about 18:1, about 2:1 to about 15:1, about 3:1 to about 12:1, about 4:1 to about 10:1, about 5:1 to about 9:1, and about 9:1), and wherein significant microbial growth is inhibited in the composition. In some embodiments, the composition comprises a taxane or a derivative thereof (such as paclitaxel, docetaxel, or ortataxel), an albumin, and an antimicrobial agent, wherein the weight ratio of the albumin to the taxane or derivative thereof in the composition is about 18:1 or less (including for example any of about 1:1 to about 18:1, about 2:1 to about 15:1, about 3:1 to about 12:1, about 4:1 to about 10:1, about 5:1 to about 9:1, and about 9:1), and wherein significant microbial growth is inhibited in the composition. In some embodiments, the poorly water soluble pharmaceutical agent (such as taxane or derivative thereof) is coated with albumin. In some embodiments, the antimicrobial agent is a chelating agent, such as any of (and in some embodiments selected from the group consisting of) edetate, citrate, pentetate, tromethamine, sorbate, ascorbate, derivatives thereof, and mixtures thereof. In some embodiments, the chelating agent is not deferoxamine (i.e., is other than deferoxamine). In some embodiments, the antimicrobial agent is a non-chelating agent, such as any of (and in some embodiments selected from the group consisting of) sulfites, benzoic acid, benzyl alcohol, chlorobutanol, paraben, derivatives thereof, and mixtures thereof. In some embodiments, the composition further comprises a sugar (such as the sugar described herein).

In some embodiments, the composition comprises a protein-associated poorly water soluble pharmaceutical agent and an antimicrobial agent, wherein significant microbial growth is inhibited in the composition. In some embodiments, the composition comprises a protein-associated taxane or a derivative thereof (such as a protein-associated paclitaxel, protein-associated docetaxel, or protein-associated ortataxel) and an antimicrobial agent, wherein significant microbial growth is inhibited in the composition. In some embodiments, the antimicrobial agent is a chelating agent, such as any of (and in some embodiments selected from the group consisting of) edetate, citrate, pentetate, tromethamine, sorbate, ascorbate, derivatives thereof, and mixtures thereof. In some embodiments, the chelating agent is not deferoxamine (i.e., is other than deferoxamine). In some embodiments, the antimicrobial agent is a non-chelating agent, such as any of (and in some embodiments selected from the group consisting of) sulfites, benzoic acid, benzyl alcohol, chlorobutanol, paraben, derivatives thereof, and mixtures thereof.

In some embodiments, the protein/pharmaceutical agent is in particulate form, which in various embodiments may be of average diameters as described herein.

In some embodiments, the composition comprises (1) particles (such as nanoparticles) comprising (in various embodiments consisting of or consisting essentially of) a poorly water soluble pharmaceutical agent and a carrier protein; and (2) an antimicrobial agent, wherein significant microbial growth is inhibited in the composition. In some embodiments, the poorly water soluble agent is coated with the carrier protein. In some embodiments, the composition comprises particles (such as nanoparticles) comprising (in various embodiments consisting of or consisting essentially of) (1) taxane or a derivative thereof (such as paclitaxel, docetaxel, or ortataxel) and carrier protein; and (2) an antimicrobial agent, wherein significant microbial growth is inhibited in the composition. In some embodiments, the taxane or a derivative thereof is coated with the carrier protein. In some embodiments, the antimicrobial agent is a chelating agent, such as any of (and in some embodiments selected from the group consisting of) edetate, citrate, pentetate, tromethamine, sorbate, ascorbate, derivatives thereof, and mixtures thereof. In some embodiments, the chelating agent is not deferoxamine (i.e., is other than deferoxamine). In some embodiments, the antimicrobial agent is a non-chelating agent, such as any of (and in some embodiments selected from the group consisting of) sulfites or their derivatives, benzoic acid, benzyl alcohol, chlorobutanol, paraben, derivatives thereof, and mixtures thereof.

In some embodiments, the composition comprises (1) particles (such as nanoparticles) comprising (in various embodiments consisting of or consisting essentially of) a poorly water soluble pharmaceutical agent and albumin; and (2) an antimicrobial agent, wherein the weight ratio of the albumin to the poorly water soluble pharmaceutical agent in the composition is about 0.0:1 to about 100:1, and wherein significant microbial growth is inhibited in the composition. In some embodiments, the composition comprises (1) particles (such as nanoparticles) comprising (in various embodiments consisting of or consisting essentially of) a poorly water soluble pharmaceutical agent and albumin; and (2) an antimicrobial agent, wherein the weight ratio of the albumin to the poorly water soluble pharmaceutical agent in the composition is about 18:1 or less (including for example any of about 1:1 to about 18:1, about 2:1 to about 15:1, about 3:1 to about 12:1, about 4:1 to about 10:1, about 5:1 to about 9:1, and about 9:1), and wherein significant microbial growth is inhibited in the composition. In some embodiments, the composition comprises (such as consists of or consists essentially of) (1) particles (such as nanoparticles) comprising taxane or a derivative thereof (such as paclitaxel, docetaxel, or ortataxel) and albumin; and (2) an antimicrobial agent, wherein the weight ratio of the albumin to the taxane or a derivative thereof in the composition is about 18:1 or less (including for example any of about 1:1 to about 18:1, about 2:1 to about 15:1, about 3:1 to about 12:1, about 4:1 to about 10:1, about 5:1 to about 9:1, and about 9:1), and wherein significant microbial growth is inhibited in the composition. In some embodiments, the poorly water soluble pharmaceutical agent (such as taxane or derivative thereof) is coated with albumin. In some embodiments, the antimicrobial agent is a chelating agent, such as any of (and in some embodiments selected from the group consisting of) edetate, citrate, pentetate, tromethamine, sorbate, ascorbate, derivatives thereof, and mixtures thereof. In some embodiments, the chelating agent is not deferoxamine (i.e., is other than deferoxamine). In some embodiments, the chelating agent is not citrate (i.e., is other than citrate). In some embodiments, the antimicrobial agent is a non-chelating agent, such as any of (and in some embodiments selected from the group consisting of) sulfites, benzoic acid, benzyl alcohol, chlorobutanol, paraben, derivatives thereof, and mixtures thereof. In some embodiments, the composition further comprises a sugar (such as the sugar described herein). In some embodiments, the poorly water soluble pharmaceutical agent is docetaxel or a derivative thereof.

In some embodiments, the composition comprises (1) particles (such as nanoparticles) comprising (in various embodiments consisting of or consisting essentially of) paclitaxel and albumin; and (2) an antimicrobial agent, wherein the weight ratio of albumin to paclitaxel (w/w) is about 0.01:1 to about 100:1, wherein significant microbial growth is inhibited in the composition. In some embodiments, the composition comprises (1) particles (such as nanoparticles) comprising (in various embodiments consisting of or consisting essentially of) paclitaxel and albumin; and (2) an antimicrobial agent, wherein the weight ratio of albumin to paclitaxel (w/w) is about 18:1 or less (including for example any of about 1:1 to about 18:1, about 2:1 to about 15:1, about 3:1 to about 12:1, about 4:1 to about 10:1, about 5:1 to about 9:1, and about 9:1), wherein significant microbial growth is inhibited in the composition. In some embodiments, the albumin to paclitaxel weight ratio is about any of 18:1 or less, 15:1 or less, 14:1 or less, 13:1 or less, 12:1 or less, 11:1 or less, 10:1 or less, 9:1 or less, 8:1 or less, 7:1 or less, 6:1 or less, 5:1 or less, 4:1 or less, and 3:1 or less. In some embodiments, the paclitaxel is coated with albumin. In some embodiments, the composition is substantially free (such as free) of Cremophor. In some embodiments, the composition comprises a stable aqueous suspension of particles (such as nanoparticles) comprising paclitaxel and albumin (such as particles of paclitaxel coated with albumin), wherein the composition further comprises an antimicrobial agent, wherein the weight ratio of albumin and the paclitaxel in the composition is about 9:1 or less, and wherein significant microbial growth is inhibited in the composition. In some embodiments, the composition comprises a dry (such as lyophilized) composition that can be reconstituted (or resuspended or rehydrated) to form generally a stable aqueous suspension of particles (such as nanoparticles) comprising paclitaxel and albumin (such as paclitaxel coated with albumin), wherein the composition further comprises an antimicrobial agent, wherein the weight ratio of albumin and the paclitaxel in the composition is about 18:1 or less (including for example any of about 1:1 to about 18:1, about 2:1 to about 15:1, about 3:1 to about 12:1, about 4:1 to about 10:1, about 5:1 to about 9:1, and about 9:1), and wherein significant microbial growth is inhibited in the composition. In some embodiments, the antimicrobial agent is a chelating agent, such as any of (and in some embodiments selected from the group consisting of) edetate, citrate pentetate, tromethamine, sorbate, ascorbate, derivatives thereof, and mixtures thereof. In some embodiments, the chelating agent is not deferoxamine (i.e., is other than deferoxamine). In some embodiments, the antimicrobial agent is a non-chelating agent, such as any of (and in some embodiments selected from the group consisting of) sulfites or their derivatives, benzoic acid, benzyl alcohol, chlorobutanol, paraben, derivatives thereof, and mixtures thereof. In some embodiments, the composition further comprises a sugar (such as the sugar described herein).

In some embodiments, the particles (such as nanoparticles) described herein have an average or mean diameter of no greater than about any of 1000, 900, 800, 700, 600, 500, 400, 300, 200, and 100 nm. In some embodiments, the average or mean diameter of the particles is no greater than about 200 nm. In some embodiments, the average or mean diameter of the particles is between about 20 nm to about 400 nm. In some embodiments, the average or mean diameter of the particles is between about 40 nm to about 200 nm. In some embodiments, the particles are sterile-filterable.

In some embodiments, the composition comprises a poorly water soluble pharmaceutical agent (such as a taxane or a derivative thereof), a carrier protein (such as albumin), and an antimicrobial agent in an amount that is effective to inhibit significant microbial growth in the composition. In some embodiments, the composition comprises a poorly water soluble pharmaceutical agent (such as a taxane or a derivative thereof), a carrier protein (such as albumin) in an amount that is effective to stabilize the poorly water soluble pharmaceutical agent in an aqueous medium, and an antimicrobial agent in an amount that is effective to inhibit significant microbial growth in the composition. In some embodiments, the composition comprises a poorly water soluble pharmaceutical agent (such as taxane or a derivative thereof), a carrier protein (such as albumin) in an amount that is effective to reduce one or more side effects of administration of the poorly water soluble pharmaceutical agent in a human, and an antimicrobial agent in an amount that is effective to inhibit significant microbial growth in the composition. In some embodiments, the antimicrobial agent is a chelating agent, such as any of (and in some embodiments selected from the group consisting of) edetate, citrate, pentetate, tromethamine, sorbate, ascorbate, derivatives thereof, and mixtures thereof. In some embodiments, the antimicrobial agent is a non-chelating agent, such as any of (and in some embodiments selected from the group consisting of) sulfites, benzoic acid, benzyl alcohol, chlorobutanol, paraben, derivatives thereof, and mixtures thereof. The specific amounts of the antimicrobial agents are further described herein below.

The compositions described herein may be a stable aqueous suspension of the poorly water soluble pharmaceutical agent, such as a stable aqueous suspension of the poorly water soluble pharmaceutical agent at a concentration of any of about 0.1 to about 100 mg/ml, about 0.1 to about 50 mg/ml, about 0.1 to about 20 mg/ml, about 1 to about 10 mg/ml, about 2 mg/ml to about 8 mg/ml, about 4 to about 6 mg/ml, and about 5 mg/ml. In some embodiments, the concentration of the poorly water soluble pharmaceutical agent is at least about any of 1.3 mg/ml, 1.5 mg/ml, 2 mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 25 mg/ml, 30 mg/ml, 40 mg/ml, and 50 mg/ml.

In some embodiments, the composition is a dry (such as lyophilized) composition that can be reconstituted, resuspended, or rehydrated to form generally a stable aqueous suspension of the poorly water soluble pharmaceutical agent. In some embodiments, the composition is a liquid (such as aqueous) composition obtained by reconstituting or resuspending a dry composition. In some embodiments, the composition is an intermediate liquid (such as aqueous) composition that can be dried (such as lyophilized).

In some embodiments, the composition is suitable for parenteral (such as intravenous) administration. In some embodiments, the composition is suitable for multidose administration. In some embodiments, the composition is sterile filterable. In some embodiments, the composition does not cause significant side effects in an individual (such as human) when administered to the individual. In some embodiments, the compositions described herein are substantially free (such as free) of surfactants. In some embodiments, the compositions described herein are substantially free (such as free of) Cremophor. The antimicrobial agent containing compositions described herein may further comprise a sugar or other lyophilization or reconstitution aids.

In some embodiments, the amount of the antimicrobial agent in the composition is below the level that induces a toxicological effect (i.e., above a clinically acceptable level of toxicity) or is at a level where a potential side effect can be controlled or tolerated when the composition is administered to the individual. In some embodiments, the antimicrobial agent is present in an amount that does not adversely affect the stability or characteristics of the carrier protein in the composition.

In another aspect, there are provided compositions (such as lyophilized compositions or intermediate liquid compositions that can be lyophilized) comprising a poorly water soluble pharmaceutical agent, a carrier protein (such as albumin), and a sugar. In some embodiments, the composition comprises (1) particles (such as nanoparticles) comprising (in various embodiments consisting of or consisting essentially of) poorly water soluble pharmaceutical agent (such as taxane or derivatives thereof) and an albumin; and (2) a sugar, wherein the weight ratio of the albumin to the poorly water soluble pharmaceutical agent in the composition is about 0.01:1 to about 100:1. In some embodiments, the composition comprises (1) particles (such as nanoparticles) comprising (in various embodiments consisting of or consisting essentially of) poorly water soluble pharmaceutical agent (such as taxane or derivatives thereof) and an albumin; and (2) a sugar, wherein the weight ratio of the albumin to the poorly water soluble pharmaceutical agent in the composition is about 18:1 or less (including for example any of about 1:1 to about 18:1, about 2:1 to about 15:1, about 3:1 to about 12:1, about 4:1 to about 10:1, about 5:1 to about 9:1, and about 9:1). In some embodiments, the poorly water soluble pharmaceutical agent is coated with albumin. In some embodiments, the composition is a dry (such as lyophilized) composition wherein the lyophilized composition can be reconstituted (or resuspended or rehydrated) to form generally a stable aqueous suspension of the poorly water soluble pharmaceutical agent, and wherein the time of reconstitution of the composition in an aqueous solution is less than that for the composition absent the sugar. In some embodiments, the concentration of sugar in the composition or a reconstituted suspension resulting from the composition is greater than about 50 mg/ml. In some embodiments, the composition further comprises an antimicrobial agent, such as antimicrobial agents described herein. In some embodiments, the poorly water soluble pharmaceutical agent is docetaxel or a derivative thereof.

In some embodiments, the invention provides a composition comprising paclitaxel, an albumin, and a sugar, wherein the weight ratio of the albumin to the paclitaxel is about 9:1 or less, and wherein the sugar in the composition or a reconstituted suspension resulting from the composition is greater than about 50 mg/ml. In some embodiments, the composition comprises (1) particles (such as nanoparticles) comprising (in various embodiments consisting of or consisting essentially of) paclitaxel and albumin; and (2) a sugar, wherein the weight ratio of albumin and the paclitaxel in the composition is about 18:1 or less (including for example any of about 1:1 to about 18:1, about 2:1 to about 15:1, about 3:1 to about 12:1, about 4:1 to about 10:1, about 5:1 to about 9:1, and about 9:1), and wherein the sugar in the composition or a reconstituted suspension resulting from the composition is greater than about 50 mg/ml.

In some embodiments, the sugar is in an amount that is effective to increase the stability of the poorly water soluble pharmaceutical agent in the composition as compared to a composition without the sugar. In some embodiments, the sugar is in an amount that is effective to improve filterability of the composition as compared to a composition without the sugar. In some embodiments, the sugar is in an amount that is effective to reduce foaming during reconstitution of the lyophilized composition as compared to a composition without the sugar.

Also provided are unit dosage forms of compositions described herein, articles of manufacture comprising the inventive compositions or unit dosage forms in suitable packaging (such as vials or vessels (including sealed vials or vessels and sterile sealed vials or vessels)), and kits comprising the compositions. The invention also provides methods of making and using these compositions as described herein.

It is to be understood that one, some, or all of the properties of the various embodiments described herein may be combined to form other embodiments of the present invention.

DETAILED DESCRIPTION OF THE INVENTION

The present invention in one aspect provides compositions, including pharmaceutical compositions, comprising a poorly water soluble pharmaceutical agent, a carrier protein, and an antimicrobial agent. The carrier protein in the composition generally makes the poorly water soluble pharmaceutical agent more readily suspendable in an aqueous medium and/or helps maintain the suspension as compared to compositions not comprising the carrier protein. The carrier protein is generally, but not necessarily, present in an amount that is sufficient to stabilize the poorly water soluble pharmaceutical agent in an aqueous suspension and/or in an amount that is effective to reduce one or more side effects of administration of the poorly water soluble pharmaceutical agent into an individual (such as a human). The antimicrobial agent is generally present in an amount that is effective to inhibit (such as delay, reduce, slow, and/or prevent) significant microbial growth in the composition. Preferably, the amount of the antimicrobial agent in the composition is below the level that induces a toxicological effect or at a level where a potential side effect can be controlled or tolerated.

In another aspect, there are provided compositions (such as lyophilized compositions or an intermediate liquid composition that can be lyophilized) comprising a poorly water soluble pharmaceutical agent, a carrier protein (such as albumin), and a sugar.

General reference to "the composition" or "compositions" includes and is applicable to compositions of the invention. The invention also provides pharmaceutical compositions comprising the components described herein.

Reference to paclitaxel herein applies to paclitaxel or its derivatives and accordingly the invention contemplates and includes both these embodiments. Reference to "paclitaxel" is to simplify the description and is exemplary. Derivatives or analogs of paclitaxel include, but are not limited to, compounds that are structurally similar to paclitaxel or are in the same general chemical class as paclitaxel, e.g., docetaxels. In some embodiments, the derivative or analog of paclitaxel retains similar biological, pharmacological, chemical and/or physical property (including, for example, functionality) of paclitaxel. Examples of paclitaxel derivatives or analogs include docetaxel and ortataxel. This same principle of description applies to other agents provided herein such as including, for example, antimicrobial agents and poorly water soluble pharmaceutical agents (such as taxane (including docetaxel, ortataxel, or other taxanes), geldanamycin, 17-allyl amino geldanamycin, thiocolchicine and its dimers, rapamycin, cyclosporine, epothilone, radicicol, and combretastatin).

It is understood that aspect and embodiments of the invention described herein include "consisting" and/or "consisting essentially of" aspects and embodiments.

Antimicrobial Agents

The term "antimicrobial agent" used herein refers to an agent that is capable of inhibiting (such as delaying, reducing, slowing, and/or preventing) the growth of one or more microorganisms. Significant microbial growth can be measured or indicated by a number of ways known in the art, such as one or more of the following: (1) microbial growth in a composition that is enough to cause one or more adverse effects to an individual when the composition is administered to the individual; (2) more than about 10-fold increase in microbial growth over a certain period of time (for example over a 24 hour period) upon extrinsic contamination (such as exposure to $10\text{-}10^3$ colony forming units at a temperature in the range of 20 to 25° C.). Other indicia of significant microbial growth are described herein.

The antimicrobial agent described herein may be effective against growth of one or more of bacteria (including both gram positive and gram negative bacteria), fungi, or molds. For example, in some embodiments, the antimicrobial agent is effective against growth of any one or more of gram positive cocci (such as *Staphylococcus aureus* and *Staphylococcus epidermidis*), fermentative gram-negative rods (such as *Klebsiella pneumoniae, Enterobacter cloaceae, Escherichia Coli, Proteus* species, and *Enterobacter gergoviae*), non-fermentative gram-negative rods (such as *Pseudomonas aeruginosa, Pseudomonas cepacia, Pseudomonas fluorescens, Pseudomonas putida, Flavobacterium,* and *Acinetobacter* species), and spore-forming bacteria (such as *Bacillus subtilis*). In some embodiments, the antimicrobial agent is effective against growth of any one or more of yeasts (such as *Candida albicans, Candida parapsilosis*) and molds (such as *Aspergillus niger,* and *Penicillium notatum*).

Other bacteria whose growth can be inhibited include, for example, *B. cereus, B. cohaerens, B. megatherium, B. plicatus, B. ubicuitarius, Corynebacterium nicotinovorans, Enterobacter aerogenes, Lactobacillus arabinosus, L. asei, Ps. Effuse,* and *Ps. Ovalis.* Other fungi whose growth can be inhibited include, for example, *Candida krusei, C. pseudotropicalis, Hansenula anomala, Pichia membranaefaciens, S. anamensis, S. cerevisiae, S. ellipsoideus, S. spec, Torula lipolytica, Willia anomala,* and *Z. nussbaumii.* Other molds whose growth can be inhibited include, for example, *Trichoderma lignorm, Fusarium spec, Gliocladium roseum, Mucor spec,* and *Penicillium glausum.*

The efficacy of the antimicrobial agents against various microorganisms can be measured by methods known in the art, such as the USP/EP preservative efficacy tests or modifications thereof. See Sutton and Porter, *PDA J. Pharm. Sci. Tech.,* 2002; 56:6, 300-311. See also U.S. Pat. Publication No. 2004/0009168. For example, growth inhibition capability of the antimicrobial agents in the final composition can be evaluated using membrane filtration techniques and broth cultures. Approximately 50-200 colony forming units (CFU) per mL of four standard organisms recommended by United States Pharcacopecia (USP) for preservative efficacy tests can be inoculated in each formulation. These four organisms are identified as: *Staphylococcus aureus* (ATCC 6538), *Escherichia coli* (ATCC 8739), *Pseudomonas aeruginosa* (ATCC 9027), and *Candida albicans* (ATCC 10231). In addition to these organisms, *S. epidermidis* (ATCC 12228) and *S. aureus* (coagulase negative, ATCC 27734) can also be tested. After inoculation of the test organisms, test formulations can be incubated at 30-35° C. The viable count for the test organism at chosen time points (such as immediately following the inoculation and after 24 hour of incubation at 30-35° C.) can be determined.

In some embodiments, the antimicrobial agent is in an amount that is effective to inhibit significant microbial growth for at least about any of 4, 8, 12, 18, 24, 36, 48, 60, 72, 84, 96, or 108, or 120 hours.

The antimicrobial agent is considered effective, for example, if the antimicrobial agent is capable of retarding the growth of microorganisms in the composition to no more greater than about 1 log increase (10 fold) in about 24 hours after extrinsic contamination. In some embodiments, the antimicrobial agent is effective if it causes at least about a 1.0 log reduction from the initial count at about 7 days, about a 3.0 log reduction at about 14 days, and/or no increase at about day 28 in the bacterial samples. In some embodiments, the antimicrobial is effective if it causes at least about a 2.0 log reduction from the initial count at about 6 hours, about a 3.0 log reduction at about 24 hours, and/or no recovery at about day 28 in the bacterial samples. In some embodiments, the antimicrobial agent is effective if it causes about a 2.0 log reduction from the initial count at about day 7 and/or no increase at about day 28 in the yeast and mold samples. In some embodiments, the antimicrobial agent is effective if it causes at least about a 1.0 log reduction from the initial count at about 24 hours, about a 3.0 log reduction at about day 7, and no increase at about day 28 in the bacterial samples. In some embodiments, the antimicrobial agent is effective if it causes about a 1.0 log reduction from the initial count at about day 14 and no increase at about day 28 in the yeast and mold samples.

In some embodiments, the amount of the antimicrobial agent in the composition is below the level that induces a toxicological effect (i.e., above a clinically acceptable level of toxicity) or at a level where a potential side effect can be controlled or tolerated when the composition is administered to an individual. Methods of determining toxicity or side effects of agents administered to an individual are generally known in the art, and depend on the particular antimicrobial agent in the composition. For example, many calcium-chelating antimicrobial agents (such as EDTA) can cause cardiac problems (such as cardiac arrhythmia) when administered to an individual at high levels. Indications of cardiac arrhythmia can thus be monitored to evaluate the toxicity effect of the calcium-chelating agent. Other indications such as anemia (for ion chelators), weight loss, and mortality can also be evaluated on animal models to determine the optimal amount of the antimicrobial agent.

In some embodiments, the antimicrobial agent is present in an amount that does not adversely affect the stability or characteristics of the carrier protein in the composition. In some embodiments, the antimicrobial agent (such as EDTA and non-chelating antimicrobial agents that are antioxidants) is present in an amount that is effective to inhibit oxidation in the composition. The specific amount of the antimicrobial agents in the composition will vary depending on the particular antimicrobial agent or agents in the composition, and are described further below in detail.

Chelating Agents

In some embodiments, the antimicrobial agent is a chelating agent. Chelating agents function as antimicrobial agents primarily by removing essential metal ions (such as calcium, zinc, magnesium, etc.) and make them unavailable for essential metabolic processes. These chelating agents are either specific to a particular metal ion (such as calcium, zinc, magnesium, etc.), or show a broad spectrum of metal ion specificity. In some embodiments, the chelating agent is a polydentate. In some embodiments, the chelating agent comprises one or more carboxylic acid groups. In some embodiments, the chelating agent is not deferoxamine. Suitable chelating agents include, but are not limited to, edetate, citrate, pentetate, tromethamine, sorbate, ascorbate, derivatives thereof, and mixtures thereof.

One antimicrobial agent contemplated herein is an edetate, i.e., ethylenediaminetetraacetic acid (EDTA) and derivatives thereof. Suitable derivatives for use in the present invention include disodium edetate, trisodium edetate, tetrasodium edetate and disodium calcium edetate. The nature of the edetate is not critical, provided that it fulfils the function of inhibiting significant growth of microorganisms for an extended time (such as at least about 24 hours). In some embodiments, the edetate is present in the compositions in a concentration of about 0.001 mg/ml to about 1 mg/ml, including for example any of 0.01 mg/ml to about 1 mg/ml, about 0.01 mg/ml to about 0.5 mg/ml, about 0.01 mg/ml to about 0.3 mg/ml, about 0.02 mg/ml to about 0.2 mg/ml, about 0.03 mg/ml to about 0.1 mg/ml, and about 0.05 mg/ml. In some embodiments, the concentration of edetate is less than about 1 mg/ml, such as less than about any of 0.9, 0.8, 0.7, 0.6, 0.5, 0.4, 0.3, 0.2, 0.1, 0.09, 0.08, 0.07, 0.06, 0.05, 0.04, 0.03, 0.02, 0.01, 0.009, 0.008, 0.007, 0.006, 0.005, 0.004, 0.003, 0.002, or 0.001 mg/ml. In some embodiments, the weight ratio of the edetate to the poorly water soluble pharmaceutical agent in the composition is about 0.002:1 to about 0.2:1, including for example about 0.002:1 to about 0.1:1, about 0.002:1 to about 0.06:1, about 0.004:1 to about 0.04:1, about 0.006:1 to about 0.02:1, and about 0.01:1. In some embodiments, the weight ratio of the edetate and the poorly water soluble pharmaceutical agent in the composition is less than about any of 02:1, 1.5:1, 0.1:1, 0.05:1, 0.01:1, and 0.005:1.

Another antimicrobial agent contemplated herein is a citrate, such as sodium citrate and citric acid. Suitable concentrations of citrate include, for example, about 0.1 mg/ml to about 200 mg/ml, about 0.2 mg/ml to about 100 mg/ml, about 0.3 mg/ml to about 50 mg/ml, about 0.5 mg/ml to about 10 mg/ml, and about 1 mg/ml to about 5 mg/ml. In some embodiments, the concentration of citrate is less than about 200 mg/ml, such as less than about any of 100, 50, 30, 20, 10, 9, 8, 7, 6, 5, 4, 3, 2, 1, 0.9, 0.8, 0.7, 0.6, 0.5, 0.4, 0.3, or 0.2 mg/ml. In some embodiments, the weight ratio of citrate to the poorly water soluble pharmaceutical agent is about 0.02:1 to about 40:1, including for example, about 0.04:1 to about 20:1, about 0.06:1 to about 10:1, about 0.1:1 to about 2:1, about 0.2:1 to about 1 mg/ml. In some embodiments, the weight ratio of the citrate to the poorly water soluble pharmaceutical agent is less than about any of 40:1, 30:1, 20:1, 10:1, 5:1, 1:1, 0.5:1, and 0.1:1. In other embodiments, the antimicrobial agent is not citrate (i.e., other than citrate).

The antimicrobial agent can also be a pentetate (including calcium trisodium pentetate). In some embodiments, the amount of pentetate is less than about 3 mg/ml (including for example less than about any of 2, 1.5, 1, 0.5, 0.3, 0.1, 0.09, 0.08, 0.7, 0.6, 0.5, 0.4, 0.3, 0.2, 0.1, and 0.05 mg/ml). For example, pentetate may be present in the range of any of about 0.005 to about 3 mg/ml, about 0.005 to about 0.1 mg/ml, or about 0.005 to about 0.05 mg/ml. In some embodiments, the weight ratio of the pentetate to the poorly water soluble pharmaceutical agent is about 0.001:1 to about 0.6:1, including for example about 0.001:1 to about 0.2:1, and about 0.01:1 to about 0.1:1. In some embodiments, the weight ratio of the pentetate to the poorly water soluble pharmaceutical agent is less than about any of 0.6:1, 0.3:1, 0.1:1, 0.05:1, and 0.01:1.

Another antimicrobial agent contemplated herein is tromethamine. Tromethamine as used herein, refers to 2-amino-2-hydroxymethyl-1,3-propanediol, also known as TRIS. In some embodiments, tromethamine is present in compositions in amounts of no more than about 2.5 mg/ml (including for example less than about any of 2.5, 2, 1.5, or 1 mg/ml). For example, tromethamine is present in the range of any of about 1.5 to about 2.5 mg/ml, such as about 2 mg/ml. Another exemplary amount of tromethamine is about 2.4 mg/ml. In some embodiments, the weight ratio of the tromethamine to the poorly water soluble pharmaceutical agent is about 0.1:1 to about 0.5:1, including for example about 0.2:1 to about 0.5:1, and about 0.2:1 to about 0.4:1. In some embodiments, the weight ratio of the tromethamine and the poorly water soluble pharmaceutical agent in the composition is less than about any of 0.5:1, 0.4:1, 0.3:1, 0.2:1, and 0.1:1.

In some embodiments, the chelating antimicrobial agent is a sorbate (such as potassium sorbate). In some embodiments, the sorbate is present in the composition in amounts of no more than about 2.5 mg/ml (including for example less than about any of 2.5, 2, 1.5, or 1 mg/ml). For example, the sorbate may be present in the amount of about 0.5 mg/ml. In some embodiments, the weight ratio of the sorbate and the poorly water soluble pharmaceutical agent in the composition is less than about any of 0.5:1, 0.4:1, 0.2:1, or 0.1:1.

In some embodiments, the chelating antimicrobial agent is an ascorbate (such as sodium ascorbate). In some embodiments, the ascorbate is present in the composition in amounts of no more than about 5 mg/ml (including for example less than about any of 2.5, 2, 1.5, or 1 mg/ml). For example, the ascorbate may be present in the amount of 1 mg/ml. In some embodiments, the weight ratio of the sorbate and the poorly water soluble pharmaceutical agent in the composition is less than about any of 1:1, 0.5:1, 0.4:1, 0.2:1, or 0.1:1.

Other suitable metal chelating antimicrobial agents and their exemplary amount include, but are not limited to, sodium formaldehyde sulfoxylate (0.1 mg/ml) and monothiolglycerol (5 mg/ml).

Non-Chelating Agents

In some embodiments, the antimicrobial agent is a not a chelating agent (i.e., it is a non-chelating antimicrobial agent), which includes, but is not limited to, sulfites, benzoic acid, benzyl alcohol, chlorobutanol, and derivatives thereof. These non-chelating antimicrobial agents function via a variety of mechanisms. In some embodiments, the non-chelating antimicrobial agent functions as a pro-oxidant. In some embodiments, the non-chelating antimicrobial agent functions as an antioxidant.

One antimicrobial agent contemplated herein is a sulfite. The term "sulfites" refers to all pharmaceutically acceptable derivatives of sulfurous acid (orthosulfurous acid) and metasulfurous acid. Suitable sulfites include, but are not limited to, sodium sulfite, sodium bisulfite, potassium sulfite, potassium bisulfite, sodium metabisulfite, potassium metabisulfite, or combinations thereof. In some embodiments, the sulfite is present from about 0.075 to about 6.6 mg/ml, including for example any of about 0.075 to about 1 mg/ml and about 0.25 mg/ml. In some embodiments, the sulfite is present in an amount that is less than about any of 5 mg/ml, 3 mg/ml, and 1 mg/ml. In some embodiments, the weight ratio of the sulfite and the poorly water soluble pharmaceutical agent is about 0.01:1 to about 1.5:1, including for example 0.02:1 to about 1:1, and about 0.05:1 to about 0.5:1. In some embodiments, the weight ratio of the sulfite and the poorly water soluble pharmaceutical agent is less than about any of 1.5:1, 1:1, 0.5:1, 0.1:1, and 0.05:1.

In some embodiments, the antimicrobial agent is a benzoic acid, benzyl alcohol, or derivatives thereof. In some embodiments, the antimicrobial agent is selected from the group consisting of benzyl alcohol, benzethonium chloride, sodium benzoate, potassium benzoate, benzyl benzoate, or various combinations thereof. In some embodiments, the amount of benzyl alcohol is in the range of about 0.175 to about 9 mg/ml, including for example any of about 0.7 to about 4.5 mg/ml, about 1.5 mg/ml and about 1 mg/ml. In some embodiments, the amount of benzyl alcohol is about 0.7 to about 9 mg/ml, optionally including an amount of EDTA of about 0.05 mg/ml. In some embodiments, the composition comprises a benzoic acid or a derivative thereof in the range of about 2 mg/ml to about 50 mg/ml, including for example any of about 1 mg/ml to about 20 mg/ml, about 2 mg/ml to about 10 mg/ml, and about 5 mg/ml. In some embodiments, the composition comprises a benzyl benzoate or sodium benzoate in the range of about 0.1 mg/ml to about 460 mg/ml, including for example about 0.5 mg/ml to about 200 mg/ml, about 1 mg/ml to about 100 mg/ml, about 1 mg/ml to about 50 mg/ml, and, 1 mg/ml. In some embodiments, the composition comprises an amount of benzethonium chloride of about 0.1 to about 1 mg/ml. In some embodiments, the weight ratio of the benzoic acid or benzyl alcohol and the poorly water soluble pharmaceutical agent in the composition is about 0.02:1 to about 150:1, including for example about 0.1:1 to about 40:1, about 0.2:1 to about 20:1, and about 0.2:1 to about 10:1. In some embodiments, the weight ratio of the benzoic acid or benzyl alcohol and the poorly water soluble agent in the composition is less than about any of 150:1, 100:1, 50:1, 10:1, 5:1, 1:1, 0.5:1, and 0.1:1.

In some embodiments, the antimicrobial agent is a chlorobutanol or derivatives thereof (such as chlorobutanol hemihydrate). Suitable amounts of chlorobutanol include, for example, about 2.5 mg/ml to about 50 mg/ml, about 5 mg/ml to about 20 mg/ml. In some embodiments, the antimicrobial agent is a phenol or a derivative thereof. Suitable amount of phenol (or a derivative thereof) include, for example, about 0.7 to about 25 mg/ml, about 1 mg/ml to about 20 mg/ml. In some embodiments, the antimicrobial agent is a cresol (such as m-cresol) or a derivative thereof. Suitable amounts of cresol (or a derivative thereof) include, for example, any of about 1.5 mg/ml to about 31 mg/ml and about 5 mg/ml to about 15 mg/ml.

In some embodiments, the non-chelating agent is paraben, which includes, but is not limited to, methyl paraben, butyl paraben, and propyl paraben. A suitable amount of paraben (such as methyl paraben) includes, for example, any of about 0.05 mg/ml to about 5 mg/ml, about 0.08 mg/ml to about 3 mg/ml, about 0.1 mg/ml to about 2 mg/ml, about 0.2 mg/ml to about 1.5 mg/ml, and about 1 mg/ml.

Other suitable antimicrobial agents include, but are not limited to, nitrates and nitrites (such as phenyl mercuric nitrate), esters of p-hydroxybenzoic acid, propionic acid and propionates, sodium diacetates, sorbic acid and sorbates, sulfur dioxide, diethylpyrocabonate (DEPC), sodium hypochlorite, sodium iodide, thimerosals, and the like.

In some embodiments, the compositions described herein comprise at least two (including for example at least any of 2, 3, 4, 5, 6, 7, 8, 9, or 10) different antimicrobial agents (such as at least two of the antimicrobial agents described herein). These antimicrobial agents can be of the same kind (e.g., different sulfite) or of different kinds (e.g., a sulfite and a benzyl alcohol). For example, combinations of methylparaben and propylparaben (1-2 mg/ml) are found to be particularly good against fungus. When multiple microbial agents are present in the composition, the effective amount of each antimicrobial agent depends on the combined effects of the antimicrobial agents. For example, if the antimicrobial agents work synergistically, the effective amount of each antimicrobial agent may be much less than what is required when the antimicrobial is present alone in a composition. In some embodiments, the composition comprises both citrate and EDTA. Citrate and EDTA are found to be particularly good against E. coli. In some embodiments, the composition comprises 200 mM citrate and EDTA. In some embodiments, the composition comprises 200 mM citrate and any of 0.001%, 0.01%, 0.1%, and 0.2% (w/v) EDTA.

Poorly Water Soluble Pharmaceutical Agent

The compositions described herein comprise poorly water soluble pharmaceutical agents. For example, the solubility in water of the poorly water soluble agent at about 20-25° C. may be less than about 10 mg/ml, including for example less than about any of 5, 2, 1, 0.5, 0.2, 0.1, 0.05, 0.02, or 0.01 mg/ml. Poorly water soluble pharmaceutical agents described herein can be, for example, anticancer or antineoplastic agents, antimicrotubule agents, immunosuppressive agents, anesthetics, hormones, agents for use in cardiovascular disorders, antiarrhythmics, antibiotics, antifungals, antihypertensives, antiasthmatics, anti-inflammatory agents, anti-arthritic agents, vasoactive agents, analgesics/antipyretics, antidepressants, antidiabetics, antifungal agents, anti-inflammatories, antianxiety agents, immunosuppressive agents, antimigraine agents, sedatives, antianginal agents, antipsychotic agents, antimanic agents, antiarthritic agents, antigout agents, anticoagulants, thrombolytic agents, antifibrinolytic agents, hemorheologic agents, antiplatelet agents, anticonvulsants, antiparkinson agents, antihistamines/antipruritics, agents useful for calcium regulation, antiviral agents, antimicrobials, anti-infectives, bronchodialators, hormones, hypoglycemic agents, hypolipidemic agents, antiulcer/antireflux agents, antinauseants/antiemetics, and oil-soluble vitamins (e.g., vitamins A, D, E, K, and the like).

In some embodiments, the poorly water soluble pharmaceutical agent is an antineoplastic agent. In some embodiments, the poorly water soluble pharmaceutical agent is a chemotherapeutic agent.

Suitable poorly water soluble pharmaceutical agents include, but are not limited to, taxanes (such as paclitaxel, docetaxel, ortataxel and other taxanes), epothilones, camptothecins, colchicines, geladanamycins, amiodarones, thyroid hormones, amphotericin, corticosteroids, propofol, melatonin, cyclosporine, rapamycin (sirolimus) and derivatives, tacrolimus, mycophenolic acids, ifosfamide, vinorelbine, vancomycin, gemcitabine, SU5416, thiotepa, bleomycin, diagnostic radiocontrast agents, and derivatives thereof. Other poorly water soluble pharmaceutical agents that are useful in the inventive compositions are described in, for example, U.S. Pat. Nos. 5,916,596, 6,096,331, 6,749,868, and 6,537,539. Additional examples of poorly water soluble pharmaceutical agents include those compounds which are poorly water soluble and which are listed in the "Therapeutic Category and Biological Activity Index" of The Merck Index (12$^{th}$ Edition, 1996).

In some embodiments, the poorly water soluble pharmaceutical agent is any of (and in some embodiments selected from the group consisting of) paclitaxel, docetaxel, ortataxel or other taxane or taxane analog, 17-allyl amino geldanamycin (17-AAG), 18-derivatized geldanamycin, camptothecin, propofol, amiodarone, cyclosporine, epothilone, radicicol, combretastatin, rapamycin, amphotericin, liothyronine, epothilone, colchicine, thiocolchicine and its dimers, thyroid hormone, vasoactive intestinal peptide, corticosteroids, melatonin, tacrolimus, mycophenolic acids, epothilones, radicicols, combretastatins, and analog or derivative thereof. In some embodiments, the poorly water soluble pharmaceutical agent is any of (and in some embodiments selected from the group consisting of) paclitaxel, docetaxel, ortataxel or other taxanes, geldanamycin, 17-allyl amino geldanamycin, thiocolchicine and its dimers, rapamycin, cyclosporine, epothilone, radicicol, and combretastatin. In some embodiments, the poorly water soluble pharmaceutical agent is rapamycin. In some embodiments, the poorly water soluble pharmaceutical agent is 17-AAG. In some embodiments, the poorly water soluble pharmaceutical agent is a thiocolchicine dimer (such as IDN5404).

In some embodiments, the poorly water soluble pharmaceutical agent is a taxane or derivative thereof, which includes, but is not limited to, paclitaxel, docetaxel and IDN5109 (ortataxel), or a derivative thereof. In some embodiments, the composition comprises a non-crystalline and/or amorphous taxane (such as paclitaxel or a derivative thereof). In some embodiments, the composition is prepared by using an anhydrous taxane (such as anhydrous docetaxel or a derivative thereof). Anhydrous docetaxel has been shown to produce more stable formulation than can be made with a hydrated docetaxel such as docetaxel trihydrate or hemi-hydrate.

Carrier Protein

The compositions described herein also comprise carrier proteins. The term "proteins" refers to polypeptides or polymers of amino acids of any length (including full length or fragments), which may be linear or branched, comprise modified amino acids, and/or be interrupted by non-amino acids. The term also encompasses an amino acid polymer that has been modified naturally or by intervention; for example, disulfide bond formation, glycosylation, lipidation, acetylation, phosphorylation, or any other manipulation or modification. Also included within this term are, for example, polypeptides containing one or more analogs of an amino acid (including, for example, unnatural amino acids, etc.), as well as other modifications known in the art. The proteins described herein may be naturally occurring, i.e., obtained or derived from a natural source (such as blood), or synthesized (such as chemically synthesized or synthesized by recombinant DNA techniques).

Examples of suitable carrier proteins include proteins normally found in blood or plasma, which include, but are not limited to, albumin, immunoglobulin including IgA, lipoproteins, apolipoprotein B, alpha-acid glycoprotein, beta-2-macroglobulin, thyroglobulin, transferin, fibronectin, factor VII, factor VIII, factor IX, factor X, and the like. In some embodiments, the carrier protein is a non-blood protein, such as casein, α-lactalbumin, and β-lactoglobulin. The carrier proteins may either be natural in origin or synthetically prepared. In some embodiments, the pharmaceutically acceptable carrier comprises albumin, such as HSA. HSA is a highly soluble globular protein of $M_r$ 65K and consists of 585 amino acids. HSA is the most abundant protein in the plasma and accounts for 70-80% of the colloid osmotic pressure of human plasma. The amino acid sequence of HSA contains a total of 17 disulphide bridges, one free thiol (Cys 34), and a single tryptophan (Trp 214). Intravenous use of HSA solution has been indicated for the prevention and treatment of hypovolumic shock (see, e.g., Tullis, *JAMA*, 237, 355-360, 460-463, (1977)) and Houser et al., *Surgery, Gynecology and Obstetrics*, 150, 811-816 (1980)) and in conjunction with exchange transfusion in the treatment of neonatal hyperbilirubinemia (see, e.g., Finlayson, *Seminars in Thrombosis and Hemostasis*, 6, 85-120, (1980)). Other albumins are contemplated, such as bovine serum albumin. Use of such non-human albumins could be appropriate, for example, in the context of use of these compositions in non-human mammals, such as the veterinary animals (including domestic pets and agricultural animals).

Human serum albumin (HSA) has multiple hydrophobic binding sites (a total of eight for fatty acids, an endogenous ligand of HSA) and binds a diverse set of drugs, especially neutral and negatively charged hydrophobic compounds (Goodman et al., *The Pharmacological Basis of Therapeutics*, 9$^{th}$ ed, McGraw-Hill New York (1996)). Two high affinity binding sites have been proposed in subdomains IIA and IIIA of HSA, which are highly elongated hydrophobic pockets with charged lysine and arginine residues near the surface which function as attachment points for polar ligand features (see, e.g., Fehske et al., *Biochem. Pharmcol.*, 30, 687-92 (1981), Vorum, *Dan. Med. Bull.*, 46, 379-99 (1999), Kragh-Hansen, *Dan. Med. Bull.*, 1441, 131-40 (1990), Curry et al., *Nat. Struct. Biol.*, 5, 827-35 (1998), Sugio et al., *Protein. Eng.*, 12, 439-46 (1999), He et al., *Nature*, 358, 209-15 (1992), and Carter et al., Adv. *Protein. Chem.*, 45, 153-203 (1994)). Paclitaxel and propofol have been shown to bind HSA (see, e.g., Paal et al., *Eur. J. Biochem.*, 268(7), 2187-91 (2001), Purcell et al., *Biochim. Biophys. Acta*, 1478(1), 61-8 (2000), Altmayer et al., *Arzneimittelforschung*, 45, 1053-6 (1995), and Garrido et al., *Rev. Esp. Anestestiol. Reanim.*, 41, 308-12 (1994)). In addition, docetaxel has been shown to bind to human plasma proteins (see, e.g., Urien et al., *Invest. New Drugs*, 14(2), 147-51 (1996)).

The carrier protein (such as albumin) in the composition generally serves as a carrier for the poorly water soluble pharmaceutical agent, i.e., the carrier protein in the composition makes the poorly water soluble pharmaceutical agent more readily suspendable in an aqueous medium or helps maintain the suspension as compared to compositions not comprising a carrier protein. This can avoid the use of toxic solvents for solubilizing the poorly water soluble pharmaceutical agent, and thereby can reduce one or more side effects of administration of the poorly water soluble pharmaceutical agent into an individual (such as a human). Thus, in some embodiments, the composition described herein is substantially free (such as free) of Cremophor, such as Cremophor EL® (BASF). In some embodiments, the composition is substantially free (such as free) of surfactants. A composition is "substantially free of Cremophor" or "substantially free of surfactant" if the amount of Cremophor or surfactant in the composition is not sufficient to cause one or more side effect(s) in an individual when the composition is administered to the individual.

In some embodiments, the carrier protein is associated with the poorly water soluble pharmaceutical agent, i.e., the composition comprises carrier protein-associated poorly water soluble pharmaceutical agent. "Association" or "associated" is used herein in a general sense and refers to the carrier protein affecting a behavior and/or property of the poorly water soluble pharmaceutical agent in an aqueous composition. For example, the carrier protein and the poorly water soluble pharmaceutical agent are considered as being "associated" if the carrier protein makes the poorly water soluble pharmaceutical agent more readily suspendable in an aqueous medium as compared to a composition without the carrier protein. As another example, the carrier protein and the poorly water soluble pharmaceutical agent is associated if the carrier protein stabilizes the poorly water soluble pharmaceutical agent in an aqueous suspension. For example, the carrier protein and the poorly water soluble pharmaceutical agent can be present in a particle or a nanoparticle, which are further described herein.

A poorly water soluble pharmaceutical agent is "stabilized" in an aqueous suspension if it remains suspended in an aqueous medium (such as without visible precipitation or sedimentation) for an extended period of time, such as for at least about any of 0.1, 0.2, 0.25, 0.5, 1, 2, 3, 4, 5, 6, 7, 8, 9, 10, 11, 12, 24, 36, 48, 60, or 72 hours. The suspension is generally, but not necessarily, suitable for administration to an individual (such as human). Stability of the suspension is generally (but not necessarily) evaluated at a storage temperature (such as room temperature (such as 20-25° C.) or refrigerated conditions (such as 4° C.)). For example, a suspension is stable at a storage temperature if it exhibits no flocculation or particle agglomeration visible to the naked eye or when viewed under the optical microscope at 1000 times, at about fifteen minutes after preparation of the suspension. Stability can also be evaluated under accelerated testing conditions, such as at a temperature that is higher than about 40° C.

The carrier protein and the poorly water soluble pharmaceutical agent in the composition can be associated in various manners. For example, in some embodiments, the carrier protein is in admixture with the poorly water soluble pharmaceutical agent. In some embodiments, the carrier protein encapsulates or entraps the poorly water soluble pharmaceutical agent. In some embodiments, the carrier protein is bound (such as non-covalently bound) to the poorly water soluble pharmaceutical agent. In some embodiments, the composition may exhibit one or more of the above aspects.

In some embodiments, the composition comprises particles (such as nanoparticles) comprising (in various embodiments consisting essentially of) a poorly water soluble pharmaceutical agent and a carrier protein. When the poorly water soluble pharmaceutical agent is in a liquid form, the particles or nanoparticles are also referred to as droplets or nanodroplets. In some embodiments, the poorly water soluble agent is coated with the carrier protein. Particles (such as nanoparticles) of poorly water soluble pharmaceutical agents have been disclosed in, for example, U.S. Pat. Nos. 5,916,596; 6,506,405; 6,537,579; and also in U.S. Pat. App. Pub. No. 2005/0004002A1.

In some embodiments, the composition comprises particles (such as nanoparticles) with an average or mean diameter of no greater than about 1000 nanometers (nm), such as no greater than about any of 900, 800, 700, 600, 500, 400, 300, 200, and 100 nm. In some embodiments, the average or mean diameters of the particles is no greater than about 200 nm. In some embodiments, the average or mean diameter of the particles is between about 20 to about 400 nm. In some embodiments, the average or mean diameter of the particles is between about 40 to about 200 nm. In some embodiments, the particles are sterile-filterable.

The particles (such as nanoparticles) described herein may be present in a dry formulation (such as lyophilized composition) or suspended in a biocompatible medium. Suitable biocompatible media include, but are not limited to, water, buffered aqueous media, saline, buffered saline, optionally buffered solutions of amino acids, optionally buffered solutions of proteins, optionally buffered solutions of sugars, optionally buffered solutions of vitamins, optionally buffered solutions of synthetic polymers, lipid-containing emulsions, and the like.

The amount of carrier protein in the composition described herein will vary depending on the poorly water soluble pharmaceutical agent and other components in the composition. In some embodiments, the composition comprises a carrier protein in an amount that is sufficient to stabilize the poorly water soluble pharmaceutical agent in an aqueous suspension, for example, in the form of a stable colloidal suspension (such as a stable suspension of nanoparticles). In some embodiments, the carrier protein is in an amount that reduces the sedimentation rate of the poorly water soluble pharmaceutical agent in an aqueous medium. For particle-containing compositions, the amount of the carrier protein also depends on the size and density of particles of the poorly water soluble pharmaceutical agent.

In some embodiments, the carrier protein is present in an amount that is sufficient to stabilize the poorly water soluble pharmaceutical agent in an aqueous suspension at a certain concentration. For example, the concentration of the poorly water soluble pharmaceutical agent in the composition is about 0.1 to about 100 mg/ml, including for example any of about 0.1 to about 50 mg/ml, about 0.1 to about 20 mg/ml, about 1 to about 10 mg/ml, about 2 mg/ml to about 8 mg/ml, about 4 to about 6 mg/ml, about 5 mg/ml. In some embodiments, the concentration of the poorly water soluble pharmaceutical agent is at least about any of 1.3 mg/ml, 1.5 mg/ml, 2 mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 25 mg/ml, 30 mg/ml, 40 mg/ml, and 50 mg/ml. In some embodiments, the carrier protein is present in an amount that avoids use of surfactants (such as Cremophor), so that the composition is free or substantially free of surfactant (such as Cremophor).

In some embodiments, the composition, in liquid form, comprises from about 0.1% to about 50% (w/v) (e.g. about 0.5% (w/v), about 5% (w/v), about 10% (w/v), about 15% (w/v), about 20% (w/v), about 30% (w/v), about 40% (w/v), or about 50% (w/v)) of carrier protein. In some embodiments, the composition, in liquid form, comprises about 0.5% to about 5% (w/v) of carrier protein.

In some embodiments, the weight ratio of carrier protein, e.g., albumin, to the poorly water soluble pharmaceutical agent is such that a sufficient amount of poorly water soluble pharmaceutical agent binds to, or is transported by, the cell. While the weight ratio of carrier protein to pharmaceutical agent will have to be optimized for different carrier protein and drug combinations, generally the weight ratio of carrier protein, e.g., albumin, to pharmaceutical agent (w/w) is about 0.01:1 to about 100:1, about 0.02:1 to about 50:1, about 0.05:1 to about 20:1, about 0.1:1 to about 20:1, about 1:1 to about 18:1, about 2:1 to about 15:1, about 3:1 to about 12:1, about 4:1 to about 10:1, about 5:1 to about 9:1, or about 9:1. In some embodiments, the carrier protein to pharmaceutical agent weight ratio is about any of 18:1 or less, 15:1 or less, 14:1 or less, 13:1 or less, 12:1 or less, 11:1 or less, 10:1 or less, 9:1 or less, 8:1 or less, 7:1 or less, 6:1 or less, 5:1 or less, 4:1 or less, and 3:1 or less.

In some embodiments, the carrier protein allows the composition to be administered to an individual (such as human) without significant side effects. In some embodiments, the carrier protein (such as albumin) is in an amount that is effective to reduce one or more side effects of administration of the poorly water soluble pharmaceutical agent to a human. The term "reducing one or more side effects of administration of the poorly water soluble pharmaceutical agent" refers to reduction, alleviation, elimination, or avoidance of one or more undesirable effects caused by the poorly water soluble pharmaceutical agent, as well as side effects caused by delivery vehicles (such as solvents that render the poorly water soluble pharmaceutical agents suitable for injection) used to deliver the poorly water soluble pharmaceutical agent. Such side effects include, for example, myelosuppression, neurotoxicity, hypersensitivity, inflammation, venous irritation, phlebitis, pain, skin irritation, peripheral neuropathy, neutropenic fever, anaphylactic reaction, venous thrombosis, extravasation, and combinations thereof. These side effects, however, are merely exemplary and other side effects, or combination of side effects, associated with various pharmaceutical agents can be reduced.

In some embodiments, the composition comprises particles (such as nanoparticles) comprising (in various embodiments consisting of or consisting essentially of) a poorly water soluble pharmaceutical agent and an albumin, wherein the weight ratio of the albumin to the poorly water soluble pharmaceutical agent (w/w) is about 0.01:1 to about 100:1, about 0.02:1 to about 50:1, about 0.05:1 to about 20:1, about 0.1:1 to about 20:1, about 1:1 to about 18:1, about 2:1 to about 15:1, about 3:1 to about 12:1, about 4:1 to about 10:1, about 5:1 to about 9:1, or about 9:1. In some embodiments, the carrier protein to pharmaceutical agent weight ratio is less than about any of 18:1 or less, 15:1 or less, 14:1 or less, 13:1 or less, 12:1 or less, 11:1 or less, 10:1 or less, 9:1 or less, 8:1 or less, 7:1 or less, 6:1 or less, 5:1 or less, 4:1 or less, and 3:1 or less. In some embodiments, the poorly water soluble pharmaceutical agent is a taxane or a derivative thereof, such as paclitaxel, docetaxel, ortataxel, or derivatives thereof.

In some embodiments, the poorly water soluble pharmaceutical agent is coated with the albumin. In some embodiments, the particles (such as nanoparticles) comprising a poorly water soluble pharmaceutical agent and albumin are suspended in an aqueous medium (such as an aqueous medium containing the albumin). For example, the composition can be a colloidal suspension of the poorly water soluble pharmaceutical agent particles (such as nanoparticles). In some embodiments, the composition is a dry (such as lyophilized) composition that can be reconstituted or suspended to a stable suspension of particles described herein. The concentration of the poorly water soluble pharmaceutical agent in the liquid composition or reconstituted composition can be dilute (0.1 mg/ml) or concentrated (100 mg/ml), including for example any of about 0.1 to about 50 mg/ml, about 0.1 to about 20 mg/ml, about 1 to about 10 mg/ml, about 2 mg/ml to about 8 mg/ml, about 4 to about 6 mg/ml, about 5 mg/ml. In some embodiments, the concentration of the poorly water soluble pharmaceutical agent is about any of 1, 2, 3, 4, 5, 6, 7, 8, 9, 10, 11, 12, 13, 14, 15, 16, 17, 18, 19, 20, 25, 30, 35, 40, 45, or 50 mg/ml. In some embodiments, the poorly water soluble pharmaceutical agent is a taxane or a derivative thereof, such as paclitaxel, docetaxel, ortataxel, or derivatives thereof.

In some embodiments, the composition comprises particles (such as nanoparticles) comprising paclitaxel, such as particles with an average or mean diameter of about 20 to about 400 nm, including for example about 40 to about 200 nm. In some embodiments, the composition comprises particles (such as nanoparticles) comprising (in various embodiments consisting essentially of) paclitaxel and albumin. In some embodiments, the paclitaxel is coated with albumin. In some embodiments, the weight ratio of albumin to paclitaxel (w/w) is any of about 0.01:1 to about 100:1, about 0.02:1 to about 50:1, about 0.05:1 to about 20:1 about 0.1:1 to about 20:1, about 1:1 to about 18:1, about 2:1 to about 15:1, about 3:1 to about 12:1, about 4:1 to about 10:1, about 5:1 to about 9:1, and about 9:1. In some embodiments, the albumin to paclitaxel weight ratio is less than about any of 18:1 or less, 15:1 or less, 14:1 or less, 13:1 or less, 12:1 or less, 11:1 or less, 10:1 or less, 9:1 or less, 8:1 or less, 7:1 or less, 6:1 or less, 5:1 or less, 4:1 or less, and 3:1 or less.

In some embodiments, the particles (such as nanoparticles) comprising paclitaxel and albumin are suspended in an aqueous medium (such as an aqueous medium containing the albumin). For example, the composition can be a colloidal suspension of the paclitaxel-containing particles (such as nanoparticles). In some embodiments, the composition is a dry (such as lyophilized composition) that can be reconstituted to an aqueous suspension of the paclitaxel-containing particles. In some embodiments, the concentration of the paclitaxel in the composition is between about 0.1 to about 100 mg/ml, including for example any of about 0.1 to about 50 mg/ml, about 0.1 to about 20 mg/ml, about 1 to about 10 mg/ml, about 2 mg/ml to about 8 mg/ml, about 4 to about 6 mg/ml, and about 5 mg/ml. In some embodiments, the concentration of the paclitaxel is at least about any of 1.3 mg/ml, 1.5 mg/ml, 2 mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 25 mg/ml, 30 mg/ml, 40 mg/ml, and 50 mg/ml.

In some embodiments, the composition comprises an albumin-containing nanoparticle formulation of paclitaxel (hereinafter referred to as Nab-paclitaxel). Nab-paclitaxel such as Capxol™ (also known as Abraxane™) has been described in U.S. Pat. No. 6,096,331. Capxol™ is a formulation of paclitaxel stabilized by human albumin USP, which can be dispersed in directly injectable physiological solution. When dispersed in a suitable aqueous medium such as 0.9% sodium chloride injection or 5% dextrose injection, Capxol™ forms a stable colloidal suspension of paclitaxel. The size (i.e., average or mean diameter) of the particles in the colloidal suspension may range from 20 nm to 8 microns with a preferred range of about 20-400 nm. Since HSA is freely soluble in water, Capxol™ can be reconstituted in a wide range of concentrations ranging from dilute (0.1 mg/ml paclitaxel) to concentrated (20 mg/ml paclitaxel), including for example about 2 mg/ml to about 8 mg/ml, about 5 mg/ml. In some embodiments, the paclitaxel concentration is about any of 1, 2, 3, 4, 5, 6, 7, 8, 9, 10, 11, 12, 13, 14, 15, 16, 17, 18, 19, and 20 mg/ml.

Sugar Containing Compositions

The present invention also provides compositions (such as pharmaceutical compositions) comprising a poorly water soluble agent, a carrier protein (such as albumin), and a sugar. The composition may further comprise an antimicrobial agent as described herein. The composition described herein include, for example, dry (such as lyophilized) compositions, liquid (such as aqueous) compositions obtained by reconstituting or resuspending a dry composition, or intermediate liquid (such as aqueous) compositions that can be dried (such as lyophilized).

"Sugar" as used herein includes, but is not limited to, monosaccharide, disaccharide, polysaccharide, and derivatives or modifications thereof. Suitable sugars for compositions described herein include, for example, mannitol, sucrose, fructose, lactose, maltose, and trehalose. In some embodiments, the sugar serves as a reconstitution enhancer which causes a lyophilized composition to dissolve or suspend in water and/or aqueous solution more quickly than the lyophilized composition would dissolve without the sugar. For example, the composition may be a dry (such as lyophilized) composition wherein the composition can be reconstituted (or resuspended or rehydrated) to a stable aqueous suspension of the poorly water soluble pharmaceutical agent, and wherein the time of reconstitution of the composition in an aqueous solution is less than that for the composition without the sugar. In some embodiments, the composition can be reconstituted (such as by mixing, tapping, or vortexing) within less than about any of 8 minutes, 5 minutes, or 2 minutes.

In some embodiments, the sugar is in an amount that is effective to increase the chemical stability of the poorly water soluble pharmaceutical agent in the composition. In some embodiments, the sugar is in an amount that is effective to improve filterability of the composition. In some embodiments, the sugar is in an amount effective to reduce foaming during reconstitution of the dry (such as lyophilized) composition. These improvements are as compared to compositions without the sugar.

In some embodiments, the concentration of sugar in a liquid suspension (such as the suspension prior to lyophilization or the reconstituted suspension) is greater than about any of 50, 60, 70, 80, 90, or 100 mg/ml. In some embodiments, the sugar is present in an amount of any of about 20 to about 100 mg/ml, about 50 mg/ml to about 100 mg/ml, about 90 mg/ml. The ratio (w/w) of the sugar to the poorly water soluble pharmaceutical agent in the composition may vary depending on the poorly water soluble pharmaceutical agent. Exemplary ratios of sugar to the poorly water soluble pharmaceutical agent (such as paclitaxel) include, for example, about any of 2:1, 3:1, 4:1, 5:1, 6:1, 7:1, 8:1, 9:1, 10:1, or more.

In some embodiments, the composition comprises (1) particles (such as nanoparticles) comprising poorly water soluble pharmaceutical agent (such as taxane or derivatives thereof) and albumin and (2) a sugar, wherein the weight ratio of albumin to pharmaceutical agent (w/w) is about 0.01:1 to about 100:1, including for example about 0.02:1 to about 50:1, about 0.05:1 to about 20:1, about 0.1:1 to about 20:1, about 1:1 to about 18:1, about 2:1 to about 15:1, about 3:1 to about 12:1, about 4:1 to about 10:1, about 5:1 to about 9:1, and about 9:1. In some embodiments, the albumin to pharmaceutical agent weight ratio is about 18:1 or less, including for example about any of 15:1 or less, 14:1 or less, 13:1 or less, 12:1 or less, 11:1 or less, 10:1 or less, 9:1 or less, 8:1 or less, 7:1 or less, 6:1 or less, 5:1 or less, 4:1 or less, and 3:1 or less. The poorly water soluble pharmaceutical agent may be coated with albumin.

In some embodiments, the invention provides a composition comprising paclitaxel, an albumin, and a sugar, wherein the weight ratio of albumin to paclitaxel (w/w) is about 0.01:1 to about 100:1, including for example about 0.02:1 to about 50:1, about 0.05:1 to about 20:1, about 0.1:1 to about 20:1, about 1:1 to about 18:1, about 2:1 to about 15:1, about 3:1 to about 12:1, about 4:1 to about 10:1, about 5:1 to about 9:1, and about 9:1. In some embodiments, the albumin to paclitaxel weight ratio is about 18:1 or less, including for example about any of 15:1 or less, 14:1 or less, 13:1 or less, 12:1 or less, 11:1 or less, 10:1 or less, 9:1 or less, 8:1 or less, 7:1 or less, 6:1 or less, 5:1 or less, 4:1 or less, and 3:1 or less. In some embodiments, the composition comprises (1) particles (such as nanoparticles) comprising paclitaxel and albumin and (2) a sugar, wherein the weight ratio of albumin to paclitaxel (w/w) is about 0.01:1 to about 100:1, including for example any of about 0.02:1 to about 50:1, about 0.05:1 to about 20:1, about 0.1:1 to about 20:1, about 1:1 to about 18:1, about 2:1 to about 15:1, about 3:1 to about 12:1, about 4:1 to about 10:1, about 5:1 to about 9:1, and about 9:1. In some embodiments, the albumin to paclitaxel weight ratio is about 18:1 or less, including for example about any of 15:1 or less, 14:1 or less, 13:1 or less, 12:1 or less, 11:1 or less, 10:1 or less, 9:1 or less, 8:1 or less, 7:1 or less, 6:1 or less, 5:1 or less, 4:1 or less, and 3:1 or less. The paclitaxel may be coated with the albumin. In some embodiments, the composition is a dry (such as lyophilized) composition which can be reconstituted (or resuspended or rehydrated) to form generally a stable aqueous suspension of the poorly water soluble pharmaceutical agent, and wherein the time of reconstitution of the composition in an aqueous solution is less than that for the composition absent the sugar. In some embodiments, the concentration of sugar in the composition or a reconstituted suspension resulting from the composition is greater than any of about 50, 60, 70, 80, 90, or 100 mg/ml. In some embodiments, the sugar is present in at a concentration of any of about 20 to about 100 mg/ml, about 50 mg/ml to about 100 mg/ml, or about 90 mg/ml.

The sugar-containing compositions described herein may further comprise one or more antimicrobial agents, such as the antimicrobial agents described herein. In addition to sugar, other reconstitution enhancers (such as those described in U.S. Pat. App. Publication No. 2005/0152979) can also be added to the compositions.

Other Components in the Compositions

The compositions described herein can include other agents, excipients, or stabilizers to improve properties of the composition. For example, to increase stability by increasing the negative zeta potential of nanoparticles, certain negatively charged components may be added. Such negatively charged components include, but are not limited to bile salts, bile acids, glycocholic acid, cholic acid, chenodeoxycholic acid, taurocholic acid, glycochenodeoxycholic acid, taurochenodeoxycholic acid, litocholic acid, ursodeoxycholic acid, dehydrocholic acid and others; phospholipids including lecithin (egg yolk) based phospholipids which include the following phosphatidylcholines: palmitoyloleoylphosphatidylcholine, palmitoyllinoleoylphosphatidylcholine, stearoyllinoleoylphosphatidylcholine stearoyloleoylphosphatidylcholine, stearoylarachidoylphosphatidylcholine, and dipalmitoylphosphatidylcholine. Other phospholipids including L-α-dimyristoylphosphatidylcholine (DMPC), dioleoylphosphatidylcholine (DOPC), distearoylphosphatidylcholine (DSPC), hydrogenated soy phosphatidylcholine (HSPC), and other related compounds. Negatively charged surfactants or emulsifiers are also suitable as additives, e.g., sodium cholesteryl sulfate and the like.

In some embodiments, the composition is suitable for administration to a human. In some embodiments, the composition is suitable for administration to a mammal such as, in the veterinary context, domestic pets and agricultural animals. There are a wide variety of suitable formulations of the inventive composition (see, e.g., U.S. Pat. Nos. 5,916,596 and 6,096,331). The following formulations and methods are merely exemplary and are in no way limiting. Formulations suitable for oral administration can comprise (a) liquid solutions, such as an effective amount of the compound dissolved in diluents, such as water, saline, or orange juice, (b) capsules, sachets or tablets, each containing a predetermined amount of the active ingredient, as solids or granules, (c) suspensions in an appropriate liquid, (d) suitable emulsions, and (e) powders. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

Formulations suitable for parenteral administration include aqueous and non-aqueous, isotonic sterile injection solutions, which can contain anti-oxidants, buffers, bacteriostats, and solutes that render the formulation compatible with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described. Injectable formulations are preferred.

Formulations suitable for aerosol administration comprise the inventive composition include aqueous and non-aqueous, isotonic sterile solutions, which can contain anti-oxidants, buffers, bacteriostats, and solutes, as well as aqueous and non-aqueous sterile suspensions that can include suspending agents, solubilizers, thickening agents, stabilizers, and preservatives, alone or in combination with other suitable components, which can be made into aerosol formulations to be administered via inhalation. These aerosol formulations can be placed into pressurized acceptable propellants, such as dichlorodifluoromethane, propane, nitrogen, and the like. They also can be formulated as pharmaceuticals for non-pressured preparations, such as in a nebulizer or an atomizer.

In some embodiments, the composition is formulated to have a pH range of about 4.5 to about 9.0, including for example pH ranges of any of about 5.0 to about 8.0, about 6.5 to about 7.5, and about 6.5 to about 7.0. In some embodiments, the pH of the composition is formulated to no less than about 6, including for example no less than about any of 6.5, 7, or 8 (such as about 8). The composition can also be made to be isotonic with blood by the addition of a suitable tonicity modifier, such as glycerol.

Also provided are articles of manufacture comprising the compositions described herein in suitable packaging. Suitable packaging for compositions described herein are known in the art, and include, for example, vials (such as sealed vials), vessels, ampules, bottles, jars, flexible packaging (e.g., sealed Mylar or plastic bags), and the like. These articles of manufacture may further be sterilized and/or sealed. Also provided are unit dosage forms comprising the compositions described herein. These unit dosage forms can be stored in a suitable packaging in single or multiple unit dosages and may also be further sterilized and sealed.

The present invention also provides kits comprising compositions (or unit dosages forms and/or articles of manufacture) described herein and may further comprise instruction(s) on methods of using the composition, such as uses further described herein. In some embodiments, the kit of the invention comprises the packaging described above. In other embodiments, the kit of the invention comprises the packaging described above and a second packaging comprising a buffer. In some embodiments, the invention provides a kit comprising (1) a composition comprising a poorly water soluble pharmaceutical agent and a carrier protein; and (2) an antimicrobial agent, wherein the poorly water soluble pharmaceutical agent/protein composition and the antimicrobial agent are present in separate packages, and wherein significant microbial growth in the composition is inhibited upon adding the antimicrobial agent to the poorly water soluble pharmaceutical agent/protein composition. In some embodiments, the kit further comprises an instruction on adding the antimicrobial agent to the pharmaceutical/protein composition. The kits described herein may further include other materials desirable from a commercial and user standpoint, including other buffers, diluents, filters, needles, syringes, and package inserts with instructions for performing any methods described herein.

Kits may also be provided that contain sufficient dosages of the poorly water soluble pharmaceutical agent (such as paclitaxel) as disclosed herein to provide effective treatment for an individual for an extended period, such as any of a week, 2 weeks, 3 weeks, 4 weeks, 6 weeks, 8 weeks, 3 months, 4 months, 5 months, 6 months, 7 months, 8 months, 9 months or more. Kits may also include multiple unit doses of the poorly water soluble pharmaceutical agent and pharmaceutical compositions and instructions for use and packaged in quantities sufficient for storage and use in pharmacies for example, hospital pharmacies and compounding pharmacies.

Methods of Making and Using the Compositions

Also provided are methods of making and using compositions described herein. For example, there is provided a method of preparing a composition comprising a poorly water soluble pharmaceutical agent (such as a taxane, for example, paclitaxel, docetaxel, or ortataxel), a carrier protein (such as albumin), and an antimicrobial agent, wherein significant microbial growth is inhibited in the composition, comprising combining (such as admixing) a composition containing a poorly water soluble pharmaceutical agent and a carrier protein with an antimicrobial agent.

Methods of making compositions containing carrier proteins and poorly water soluble pharmaceutical agents are known in the art. For example, nanoparticles containing poorly water soluble pharmaceutical agents (such as paclitaxel) and carrier protein (such as albumin) can be prepared under conditions of high shear forces (e.g., sonication, high pressure homogenization, or the like). These methods are disclosed in, for example, U.S. Pat. Nos. 5,916,596; 6,506,405; and 6,537,579 and also in U.S. Pat. Pub. No. 2005/0004002A1.

Briefly, the poorly water soluble drug (such as docetaxel) is dissolved in an organic solvent, and the solution can be added to a human serum albumin solution. The mixture is subjected to high pressure homogenization. The organic solvent can then be removed by evaporation. The dispersion obtained can be further lyophilized. Suitable organic solvent include, for example, ketones, esters, ethers, chlorinated solvents, and other solvents known in the art. For example, the organic solvent can be methylene chloride and chloroform/ethanol (for example with a ratio of 1:9, 1:8, 1:7, 1:6, 1:5, 1:4, 1:3, 1:2, 1:1, 2:1, 3:1, 4:1, 5:1, 6:1, 7:1, 8:1, or 9:1).

The antimicrobial agent can either be admixed with the poorly water soluble pharmaceutical agent and/or the carrier protein during preparation of the poorly water soluble pharmaceutical agent/carrier protein composition, or added after the poorly water soluble pharmaceutical agent/carrier protein composition is prepared. For example, the antimicrobial agent can be added along with an aqueous medium used to reconstitute/suspend the poorly water soluble pharmaceutical agent/carrier protein composition or added to an aqueous suspension of the carrier protein-associated poorly water soluble pharmaceutical agent. In some embodiments, the antimicrobial agent is admixed with the poorly water soluble pharmaceutical agent/carrier protein composition prior to lyophilization. In some embodiments, the antimicrobial agent is added to the lyophilized pharmaceutical agent/carrier protein composition.

In some embodiments when the addition of the antimicrobial agent changes the pH of the composition, the pH in the composition are generally (but not necessarily) adjusted to a desired pH. Exemplary pH values of the compositions include, for example, in the range of about 5 to about 8.5. In some embodiments, the pH of the composition is adjusted to no less than about 6, including for example no less than any of about 6.5, 7, or 8 (such as about 8).

Also provided are methods of making pharmaceutical compositions comprising combining any of the compositions described herein (including those above) with a pharmaceutically acceptable excipient.

Also provided herein are methods of using the compositions of the present invention. In some embodiments, there is provided a method for treating a disease or condition that is responsive to a poorly water soluble pharmaceutical agent comprising administering a composition comprising an effective amount of a poorly water soluble pharmaceutical agent, a carrier protein, and an antimicrobial agent, wherein significant microbial growth is inhibited in the composition. For example, in some embodiments, there is provided a method of treating cancer in an individual (such as human) comprising administering to the subject a composition comprising an effective amount of a poorly water soluble antineoplastic agent (such as taxane), a carrier protein, and an antimicrobial agent, wherein significant microbial growth is inhibited in the composition. In some embodiments, the antimicrobial agent is in an amount that is sufficient to inhibit significant microbial growth in the composition. In some embodiments, the antimicrobial agent in the composition is further in an amount that does not cause any toxicological effects when the composition is administered into an individual (such as human).

The term "effective amount" used herein refers to an amount of a compound or composition sufficient to treat a specified disorder, condition or disease such as ameliorate, palliate, lessen, and/or delay one or more of its symptoms. In reference to cancers or other unwanted cell proliferation, an effective amount comprises an amount sufficient to cause a tumor to shrink and/or to decrease the growth rate of the tumor (such as to suppress tumor growth). In some embodiments, an effective amount is an amount sufficient to delay development. In some embodiments, an effective amount is an amount sufficient to prevent occurrence and/or recurrence. An effective amount can be administered in one or more administrations.

Cancers to be treated by compositions described herein (such as a composition comprising an antineoplastic agent such as taxane, rapamycin, and 17-AAG) include, but are not limited to, carcinoma, lymphoma, blastoma, sarcoma, and leukemia. Examples of cancers that can be treated by compositions described herein include, but are not limited to, squamous cell cancer, lung cancer (including small cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, heptoma, breast cancer, colon cancer, melanoma, endometrical or uterine carcinoma, salivary gland carcinoma, kidney or renal cancer, liver cancer, prostate cancer, vulval cancer, thyroid cancer, hepatic carcinoma, head and neck cancer, colorectal cancer, rectal cancer, soft-tissue sarcoma, Kaposi's sarcoma, B-cell lymphoma (including low grade/follicular non-Hodgkin's lymphoma (NHL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, mantle cell lymphoma, AIDS-related lymphoma, and Waldenstrom's macroglobulinemia), chronic lymphocytic leukemia (CLL), acute lymphoblastic leukemia (ALL), myeloma, Hairy cell leukemia, chronic myeloblastic leukemia, and post-transplant lymphoproliferative disorder (PTLD), as well as abnormal vascular proliferation associated with phakomatoses, edema (such as that associated with brain tumors), and Meigs' syndrome. In some embodiments, there is provided a method of treating metastatic cancer (that is, cancer that has metastasized from the primary tumor). In some embodiments, there is provided a method of reducing cell proliferation and/or cell migration. In some embodiments, there is provided a method of treating hyperplasia.

In some embodiments, there are provided methods of treating cancer at advanced stage(s). In some embodiments, there are provided methods of treating breast cancer (which may be HER2 positive or HER2 negative), including, for example, advanced breast cancer, stage IV breast cancer, locally advanced breast cancer, and metastatic breast cancer. In some embodiments, the cancer is lung cancer, including, for example, non-small cell lung cancer (NSCLC, such as advanced NSCLC), small cell lung cancer (SCLC, such as advanced SCLC), and advanced solid tumor malignancy in the lung. In some embodiments, the cancer is ovarian cancer, head and neck cancer, gastric malignancies, melanoma (including metastatic melanoma), colorectal cancer, pancreatic cancer, and solid tumors (such as advanced solid tumors). In some embodiments, the cancer is any of (and in some embodiments selected from the group consisting of) breast cancer, colorectal cancer, rectal cancer, non-small cell lung cancer, non-Hodgkins lymphoma (NHL), renal cell cancer, prostate cancer, liver cancer, pancreatic cancer, soft-tissue sarcoma, Kaposi's sarcoma, carcinoid carcinoma, head and neck cancer, melanoma, ovarian cancer, mesothelioma, gliomas, glioblastomas, neuroblastomas, and multiple myeloma. In some embodiments, the cancer is a solid tumor.

Individual suitable for receiving these compositions depend on the nature of the poorly water soluble pharmaceutical agent, as well as the disease/condition/disorder to be treated and/or prevented. Accordingly, the term individual includes any of vertebrates, mammals, and humans. In some embodiments, the individual is a mammal, including, but not limited to, human, bovine, equine, feline, canine, rodent, or primate. In some embodiments, the individual is human.

The compositions described herein can be administered alone or in combination with other pharmaceutical agents, including poorly water soluble pharmaceutical agents. For example, when the composition contains a taxane (such as paclitaxel), it can be co-administered with one or more other chemotherapeutic agents including, but are not limited to, carboplatin, Navelbine® (vinorelbine), anthracycline (Doxil), lapatinib (GW57016), Herceptin, gemcitabine (Gemzar®), capecitabine (Xeloda®), alimta, cisplatin, 5-fluorouracil, epirubicin, cyclophosphamide, avastin, Velcade®, etc. In some embodiments, the taxane composition is co-administered with a chemotherapeutic agent selected from the group consisting of antimetabolites (including nucleoside analogs), platinum-based agents, alkylating agents, tyrosine kinase inhibitors, anthracycline antibiotics, vinca alkloids, proteasome inhibitors, macrolides, and topoisomerase inhibitors. These other pharmaceutical agents can be present in the same composition as the drug (such as taxane), or in a separate composition that is administered simultaneously or sequentially with the drug (such as taxane)-containing composition. Combination therapy methods using nanoparticle formulations of taxane with other agents (or therapeutic methods) have been described in International Patent Application No. PCT/US2006/006167.

The dose of the inventive composition administered to an individual (such as human) will vary with the particular composition, the method of administration, and the particular disease being treated. The dose should be sufficient to effect a desirable response, such as a therapeutic or prophylactic response against a particular disease. For example, the dosage of paclitaxel in the composition can be in the range of 100-400 mg/m$^2$ when given on a 3 week schedule, or 50-250 mg/m$^2$ when given on a weekly schedule. In addition, if given in a metronomic regimen (e.g., daily or a few times per week), the dosage may be in the range of about 5-75 mg/m$^2$.

The compositions described herein can be administered to an individual (such as human) via various routes, including, for example, intravenous, intra-arterial, intrapulmonary, oral, inhalation, intravesicular, intramuscular, intra-tracheal, subcutaneous, intraocular, intrathecal, transmucosal, and transdermal. For example, the inventive composition can be administered by inhalation to treat conditions of the respiratory tract. The composition can be used to treat respiratory conditions such as pulmonary fibrosis, broncheolitis obliterans, lung cancer, bronchoalveolar carcinoma, and the like.

Also provided herein are methods of reducing side effects associated with administration of a poorly water soluble pharmaceutical agent to a human, comprising administering to a human a pharmaceutical composition comprising the poorly water soluble pharmaceutical agent, a carrier protein, and an antimicrobial agent, wherein significant microbial growth is inhibited in the composition. For example, the invention provides methods of reducing various side effects associated with administration of the poorly water soluble pharmaceutical agent, including, but not limited to, myelosuppression, neurotoxicity, hypersensitivity, inflammation, venous irritation, phlebitis, pain, skin irritation, peripheral neuropathy, neutropenic fever, anaphylactic reaction, hematologic toxicity, and cerebral or neurologic toxicity, and combinations thereof. In some embodiments, there is provided a method of reducing hypersensitivity reactions associated with administration of the poorly water soluble pharmaceutical agent, including, for example, severe skin rashes, hives, flushing, dyspnea, tachycardia, and others. In some embodiments, the antimicrobial agent is present in an amount that is effective to inhibit significant microbial growth in the pharmaceutical composition. In some embodiments, the antimicrobial agent in the composition is further in an amount that does not cause any toxicological effects or at a level where a potential side effect can be controlled or tolerated when the composition is administered into an individual.

In addition, there is provided a method of increasing shelf-life of a liquid composition comprising a poorly water soluble pharmaceutical agent and a carrier protein. For example, in some embodiments, the invention provides a method of keeping a composition (such as a pharmaceutical composition) comprising a poorly water soluble pharmaceutical agent and a carrier protein preserved against microbial growth (i.e., sterile or substantially free of significant microbial growth) for at least 24 hours in an aqueous medium, comprising adding to the composition an antimicrobial agent in an amount that is effective to inhibit significant microbial growth in the composition. In some embodiments there is provided methods of inhibiting microbial growth in a composition (particularly in a pharmaceutical composition) comprising a carrier protein and a poorly water soluble pharmaceutical agent, comprising adding to the composition an antimicrobial agent in an amount that is effective to inhibit significant microbial growth in the composition.

The antimicrobial agent can either be admixed with the poorly water soluble pharmaceutical agent and/or the carrier protein during preparation of the poorly water soluble pharmaceutical agent/carrier protein composition, or added along with an aqueous medium used to reconstitute the pharmaceutical/carrier protein composition. In some embodiments, methods for keeping a composition preserved against microbial growth (i.e., sterile or substantially free of significant microbial growth) for at least any of 24, 36, 48, 60, 72, 84, or 96 hours are provided.

In a further aspect of the invention is provided use of the compositions described herein in the manufacture of a medicament. Particularly, the manufacture of a medicament for use in the treatment of conditions described herein. Further, the pharmaceutical composition thereof, variously described herein, are also intended for use in the manufacture of a medicament for use in treatment of the conditions and, in accordance with the methods, described herein, unless otherwise noted.

The following Examples are provided to illustrate, but not limit, the invention.

Example 1

This example provides formulations of paclitaxel/albumin and preservatives. The compositions are prepared essentially as described in U.S. Pat. Nos. 5,439,686 and 5,916,596. Briefly, paclitaxel is dissolved in an organic solvent (such as methylene chloride or a chloroform/ethanol mixture), and the solution is added to a human serum albumin solution. A suitable amount of an antimicrobial agent is then added to the mixture. The mixture is homogenized for 5 minutes at low RPM to form a crude emulsion, and then transferred into a high pressure homogenizer. The emulsification is performed at 9000-40,000 psi while recycling the emulsion for at least 5 cycles. The resulting system is transferred into a rotary evaporator, and the organic solvent is rapidly removed at 40° C., at reduced pressure (30 mm Hg) for 20-30 minutes. The dispersion is then further lyophilized for 48 hours. The resulting cake can be easily reconstituted to the original dispersion by addition of sterile water or saline, which may contain additional antimicrobial agent(s).

Exemplary formulations of compositions that can be prepared are provided below (only concentrations of paclitaxel, human albumin, and the antimicrobial agent are provided):

Formulation 1: 5 mg/ml paclitaxel; 56 mg/ml human albumin; 0.25 ml sodium metabisulfite Formulation 2: 5 mg/ml paclitaxel; 56 mg/ml human albumin; 0.05 mg/ml disodium edetate Formulation 3: 5 mg/ml paclitaxel; 56 mg/ml human albumin; 0.5 mg/ml potassium sorbate Formulation 4: 5 mg/ml paclitaxel; 56 mg/ml human albumin; 1 mg/ml sodium benzoate Formulation 5: 7 mg/ml paclitaxel; 56 mg/ml human albumin; 1 mg/ml sodium ascorbate Formulation 6: 7 mg/ml paclitaxel; 56 mg/ml human albumin; 1 mg/ml methyl paraben Formulation 7: 7 mg/ml paclitaxel; 56 mg/ml human albumin; 1 mg/ml benzyl alcohol Example 2

This example demonstrates how to determine the effectiveness of the antimicrobial agents in a composition described in Example 1.

Growth inhibition capabilities of the antimicrobial agents in the formulations described in Example 1 are evaluated using membrane filtration techniques and broth cultures. Approximately 50-200 colony forming units (CFU) per mL of four standard organisms recommended by United States Pharcacopecia (USP) for preservative efficacy tests is inoculated in each formulation. These four organisms are identified as: *Staphylococcus aureus* (ATCC 6538), *Escherichia coli* (ATCC 8739), *Pseudomonas aeruginosa* (ATCC 9027), and *Candida albicans* (ATCC 10231). In addition to these organisms, *S. epidermidis* (ATCC 12228) and *S. aureus* (coagulase negative, ATCC 27734) can also be tested. After inoculation of the test organisms, test formulations are incubated at 30-35° C. The viable counts for the test organism at chosen time points (such as immediately following the inoculation and after 24 hour of incubation at 30-35° C.) are determined.

The antimicrobial agent in the formulation is considered effective if the antimicrobial agent is capable of retarding the growth of microorganisms in the composition to no more greater than 1 log increase (10 fold) in 24 hours after extrinsic contamination.

Example 3

This example demonstrates improved reconstitution time in sugar-containing formulations of paclitaxel and albumin. The compositions were prepared essentially as described in U.S. Pat. Nos. 5,439,686 and 5,916,596, in the presence or absence of sugar. Briefly, paclitaxel was dissolved in a chloroform/ethanol (1:1) mixture, and the solution was added to a human serum albumin solution. The mixture was homogenized for 5 minutes at low RPM to form a crude emulsion, and then transferred into a high pressure homogenizer. The emulsification was performed at 9000-40,000 psi while recycling the emulsion for at least 5 cycles. The resulting system was transferred into a rotary evaporator, and chloroform/ethanol was rapidly removed at 40° C., at reduced pressure (30 mm Hg) for 20-30 minutes. The dispersion was then further lyophilized for 48 hours. The resulting cake was easily reconstituted to the original dispersion by addition of sterile water or saline, which may contain additional antimicrobial agent(s).

Sugar was added either in the human serum albumin solution or added to the dispersion prior to lyophilization.

Antimicrobial agents were not added in this particular experiment, but may be added.

The following formulations were prepared:

Formulation 1: The suspension prior to lyophilization contained 5 mg/ml paclitaxel; 56 mg/ml human albumin; 10 mg/ml mannitol. The suspension was filled into vials with 250 mg paclitaxel per vial.

Formulation 2: The suspension prior to lyophilization contained 5 mg/ml paclitaxel; 56 mg/ml human albumin; 10 mg/ml sucrose. The suspension was filled into vials with 250 mg paclitaxel per vial.

Formulation 3: The suspension prior to lyophilization contained 7 mg/ml paclitaxel; 56 mg/ml human albumin; 90 mg/ml sucrose. The suspension was filled into vials with 300 mg paclitaxel per vial.

Formulation 4: The suspension prior to lyophilization contained 7 mg/ml paclitaxel; 56 mg/ml human albumin; 50 mg/ml mannitol. The suspension was filled into vials with 300 mg paclitaxel per vial.

Formulation 5: The suspension prior to lyophilization contained 7 mg/ml paclitaxel; 56 mg/ml human albumin. The suspension was filled into vials with 300 mg paclitaxel per vial.

Lyophilized products of formulations 3 and 4 reconstituted in less than 2 minutes. The reconstitution times for lyophilized products of formulations 1, 2 and 5 were similar and between about 8-12 minutes. It was surprisingly found that 10 mg/ml sugars were not sufficient to significantly decrease reconstitution time for nab-paclitaxel. About 50-90 mg/ml sugars were required to reduce reconstitution time.

Example 4

This example further demonstrates advantageous properties of sugar-containing paclitaxel/albumin formulations.

In one experiment, composition of paclitaxel and albumin (nab-paclitaxel) was prepared with and without the presence of sugars as described above. Lyophilized vials of albumin-paclitaxel were prepared containing 300 mg per vial for both the formulations. The sugar-based formulation contained sucrose at a concentration of 90 mg/ml. The lyophilized products were subject to accelerated stability conditions at 55° C. for up to 30 days. The percent impurity 7-epitaxol was determined in case of each of the formulation and at zero time was approximately 0.1%. At 15 days and 30 days at 55° C., the level of impurity for the sugar-free formulation was found to be 0.6% and 0.8% respectively and the level of impurity for the sugar-based formulation was found to be 0.4% and 0.6% respectively. Based on the surprisingly lower impurity generation in the sugar-based formulation, its shelf life should be substantially longer than the sugar-free formulation.

In another experiment, approximately 1500 ml of the liquid suspension of each formulation containing approximately 7 mg/ml of paclitaxel, 56 mg/ml of human albumin, and 90 mg/ml sucrose were subject to filtration through a series of filters with a 0.2 µm final filter (200 cm$^2$ EKV capsule). The filterability of each formulation was assessed based on the amount of volume of nanoparticle suspension filterable through the filter. For the sugar-free formulation, the maximum volume filterable was 1300 ml at which point the filtration pressure increased beyond 25 psi indicating clogging or saturation of the filter membrane. For the sugar-based formulation, substantially increased filterability was noted with no pressure increase for 1500 ml filtered. This surprisingly demonstrates that the sugar-based nab-paclitaxel formulation is filtered more readily with minimal potency loss as compared to the formulation without sugars.

Example 5

This example demonstrates that nab-formulations may serve as growth media for microorganisms in case of adventitious contamination. The formulations contained 5 mg/ml of docetaxel, paclitaxel, and 17-AAG, respectively.

Four microorganism strains were used in the experiment: E. coli (ATCC Lot #97-08/Lot #483284); S. aureus (ATCC Lot #1836394/Lot #485823); C. albicans (ATCC Lot #98-01A/Lot #443131); P. aeruginosa (ATCC Lot #378667/Lot #484882).

100-600 µl (approx. 100-200 CFU/ml) of each strain was inoculated in 2 ml of testing batch sample tube (See Table 1, each sample was duplicated) and 2 ml TSB as control. Tryptic Soy Agar (TSA) plates were inoculated with 10% of the samples (20 drops of a 10 µl sterile disposable loop), duplicated for each sample. TSA plates were incubated aerobically at 25° C.±1° C. in the temperature controlled incubator. The colony counts for the test organism and the CFU/ml were determined at 0 hour, 24 hours and 48 hours post microbial inoculation.

The formulation is scored as "Yes" (i.e., the formulation passed the test) if the formulation shows no more than 10-fold increase in microbial growth over a 24 hour period or a 48 hour period.

TABLE 1

| Formulation | Microbial growth at 48 hours post innoculation | | | |
|---|---|---|---|---|
| | E. coli | P. aeruginosa | S. aureus | C. albicans |
| Nab-docetaxel w/citrate (200 mM citrate, 300 mM NaCl) | N | Y | Y | Y |
| Nab-docetaxel w/o citrate | N | N | N | N |
| Abraxane | N | N | N | N |
| Nab-17-AAG | N | N | Y | N |

Pass=Yes (Y) or No (N).

Nab-paclitaxel (nanoparticle albumin formulation of paclitaxel) without antimicrobial agents (Abraxane), nab-docetaxel (nanoparticle albumin formulation of docetaxel) without antimicrobial agents and nab-17AAG (nanoparticle albumin formulation of 17-AAG) without antimicrobial agent all showed substantial bacterial growth (>10 fold) over a period of either 24 or 48 hours for at least 3 of the 4 bacterial strains tested. See Table 1. This confirms that adventitious contamination of a nab-formulation without any growth inhibitors can result >10-fold increase in microorganism growth over 24 or 48 hours.

Nab-docetaxel with 200 mM citrate, on the other hand, showed microbial suppression at 24 and 48 hours except in the case of E. coli. This was remedied with the addition of EDTA. EDTA supplementation to nab-docetaxel with citrate at any of 0.001%, 0.01%, 0.1% and 0.2% (w/v) suppressed E. coli growth completely.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

What is claimed is:

1. A composition comprising: a) nanoparticles comprising a taxane and albumin, b) an edetate, and c) sucrose, wherein the composition has no more than about 10-fold increase in microbial growth over a 24 hour period upon exposure to 10-10$^3$ colony forming units at a temperature in the range of 20 to 25° C.

2. The composition of claim 1, wherein the weight ratio of albumin to the taxane in the composition is about 18:1 or less.

3. The composition of claim 1, wherein the composition comprises nanoparticles of the taxane coated with the albumin.

4. The composition of claim 3, wherein the nanoparticles in the composition have an average diameter of no greater than about 200 nm.

5. The composition of claim 4, wherein the composition is sterile filterable.

6. The composition of claim 1, wherein the composition is an aqueous suspension of the taxane at a concentration of about 0.1 to about 20 mg/ml.

7. The composition of claim 1, wherein the composition is a lyophilized composition that can be reconstituted to an aqueous suspension of the taxane at a concentration of about 0.1 to about 20 mg/ml.

8. The composition of claim 1, wherein the composition is suitable for parenteral administration.

9. The composition of claim 1, wherein the composition is substantially free of polyoxyethylated castor oil.

10. The composition of any of claims 1, 2-3 and 4-9, wherein the amount of the edetate in the composition does not cause a toxicological effect when the composition is administered into an individual.

11. The composition of claim 1, wherein the composition edetate is EDTA.

12. The composition of claim 11, wherein the composition further comprises citrate.

13. The composition of claim 1, wherein the taxane is paclitaxel.

14. The composition of claim 11, wherein the taxane is paclitaxel.

15. A method of treating cancer in an individual comprising administering to the individual an effective amount of a composition according to any of claims 1, 2-3 and 4-9.

16. The method of claim 15, wherein the amount of the edetate in the composition does not cause a toxicological effect when the composition is administered into an individual.

17. A method of preserving a composition comprising: a) nanoparticles comprising a taxane and albumin, and b) sucrose against significant microbial growth comprising adding to the composition an edetate in an amount that is effective to prevent more than about 10-fold increase in microbial growth over a 24 hour period upon exposure to $10-10^3$ colony forming units at a temperature in the range of 20 to 25° C.

18. The composition of claim 1, wherein the composition is a dry composition.

19. The composition of claim 18, wherein the dry composition can be reconstituted to a stable aqueous suspension of the taxane and wherein the time of reconstitution of the composition is less than that for the composition absent the sucrose.

20. The composition of claim 19, wherein the concentration of sucrose in the reconstituted suspension is greater than about 50 mg/ml.

21. The composition of claim 9, wherein the composition is free of polyoxyethylated castor oil.

\* \* \* \* \*